(12) United States Patent
Zhao

(10) Patent No.: US 8,420,110 B2
(45) Date of Patent: Apr. 16, 2013

(54) DRUG COATED EXPANDABLE DEVICES

(75) Inventor: Jonathon Z. Zhao, Belle Mead, NJ (US)

(73) Assignee: Cordis Corporation

( * ) Notice: Subject to any disclaimer, the term of this patent is extended or adjusted under 35 U.S.C. 154(b) by 137 days.

(21) Appl. No.: 12/784,572

(22) Filed: May 21, 2010

(65) Prior Publication Data

US 2010/0233236 A1 Sep. 16, 2010

Related U.S. Application Data

(63) Continuation-in-part of application No. 12/059,291, filed on Mar. 31, 2008, now Pat. No. 8,003,122.

(51) Int. Cl.
*A61F 2/00* (2006.01)

(52) U.S. Cl.
USPC .......................... 424/423; 623/1.12; 623/1.42

(58) Field of Classification Search .................. None
See application file for complete search history.

(56) References Cited

U.S. PATENT DOCUMENTS

| | | | |
|---|---|---|---|
| 3,576,883 A | 4/1971 | Neuworth |
| 3,576,886 A | 4/1971 | Neuworth |
| 3,862,332 A | 1/1975 | Barnhart et al. |
| 3,929,992 A | 12/1975 | Sehgal et al. |
| 3,959,078 A | 5/1976 | Guire |
| 4,350,160 A | 9/1982 | Kolesov et al. |
| 4,366,819 A | 1/1983 | Kaster |
| 4,368,736 A | 1/1983 | Kaster |
| 4,624,257 A | 11/1986 | Berggren et al. |
| 4,722,906 A | 2/1988 | Guire |
| 4,733,665 A | 3/1988 | Palmaz |
| 4,739,762 A | 4/1988 | Palmaz |
| 4,776,337 A | 10/1988 | Palmaz |
| 4,814,470 A | 3/1989 | Colin et al. |
| 4,857,653 A | 8/1989 | Colin et al. |
| 4,917,090 A | 4/1990 | Berggren et al. |
| 4,917,091 A | 4/1990 | Berggren et al. |
| 4,942,184 A | 7/1990 | Haugwitz et al. |
| 4,984,060 A | 1/1991 | Ohmi et al. |
| 5,059,699 A | 10/1991 | Hingston et al. |
| 5,200,534 A | 4/1993 | Rao |
| 5,202,448 A | 4/1993 | Carver et al. |
| 5,229,172 A | 7/1993 | Cahalan et al. |
| 5,229,529 A | 7/1993 | Ueno et al. |
| 5,234,447 A | 8/1993 | Kaster et al. |
| 5,248,796 A | 9/1993 | Chen et al. |
| 5,252,805 A | 10/1993 | Nakata et al. |
| 5,254,580 A | 10/1993 | Chen et al. |
| 5,272,171 A | 12/1993 | Neda et al. |
| 5,274,137 A | 12/1993 | Nicolaou et al. |
| 5,278,324 A | 1/1994 | Kingston et al. |
| 5,279,949 A | 1/1994 | Nair |
| 5,283,253 A | 2/1994 | Holton et al. |
| 5,294,637 A | 3/1994 | Chen et al. |
| 5,294,997 A | 3/1994 | Ogura et al. |
| 5,300,638 A | 4/1994 | Farina et al. |
| 5,308,641 A | 5/1994 | Cahalan et al. |
| 5,339,906 A | 8/1994 | Fox et al. |
| 5,350,800 A | 9/1994 | Verhoeven et al. |
| 5,350,866 A | 9/1994 | Holton et al. |
| 5,362,831 A | 11/1994 | Mongelli et al. |
| 5,380,751 A | 1/1995 | Chen |
| 5,395,850 A | 3/1995 | Roth |
| 5,411,984 A | 5/1995 | Kingston et al. |
| 5,412,092 A | 5/1995 | Rey et al. |
| 5,415,938 A | 5/1995 | Cahalan et al. |
| 5,422,364 A | 6/1995 | Nicolaou |
| 5,440,056 A | 8/1995 | Klein et al. |
| 5,516,770 A | 5/1996 | Waranis et al. |
| 5,530,006 A * | 6/1996 | Waranis et al. ............... 514/291 |
| 5,837,313 A | 11/1998 | Ding et al. |
| 5,891,845 A | 4/1999 | Myers |
| 5,924,997 A | 7/1999 | Campbell |
| 6,099,562 A | 8/2000 | Ding et al. |
| 6,120,636 A | 9/2000 | Nilsen et al. |
| 6,136,846 A | 10/2000 | Rubinfeld et al. |
| 6,153,252 A | 11/2000 | Hossainy et al. |
| 6,241,762 B1 | 6/2001 | Shanley |
| 6,248,363 B1 | 6/2001 | Patel et al. |
| 6,293,967 B1 | 9/2001 | Shanley |
| 6,319,943 B1 | 11/2001 | Joshi et al. |
| 6,425,898 B1 | 7/2002 | Wilson et al. |
| 6,451,339 B2 | 9/2002 | Patel et al. |
| 6,458,373 B1 | 10/2002 | Lambert et al. |
| 6,509,370 B1 | 1/2003 | Joshi-Hangal et al. |

(Continued)

FOREIGN PATENT DOCUMENTS

| | | |
|---|---|---|
| EP | 000153 A1 | 1/1979 |
| EP | 041795 B1 | 12/1981 |

(Continued)

OTHER PUBLICATIONS

U.S. Appl. No. 09/948,987, See US Patent 6,764,607.
Anderson, T. J., et al., "The Effect of Cholesterol-Lowering and Antioxidant Therapy on Endothelium-Dependent Coronary Vasomotion", The New England Journal of Medicine, vol. 332, No. 8, pp. 488-493, Feb. 23, 1995.
Ajroldi, G., et al., "Fluoroelastomers-Dependence of Relaxation Phenomena on Composition", Polymer (1989) vol. 30 pp. 218-2187.
Bendeck, MP, et al., "Smooth Muscle Cell Migration and Matrix Metalloproteinase Expression After Arterial Injury in the Rat", Circ Res 539-545, 1994.
Berk, BC et al., "Pharmacologic Roles of Heparin and Glucocorticoids to Prevent Restenosis After Coronary Angioplasty", J Am Coll Cardiol., 17(6 Suppl B): 111B-117B, 1991.
Campbell and Campbell, "Cell Biology of Smooth Muscle in Culture: Implications for Atherogenesis", Inter. Angio, vol. 6 (1987), pp. 73-79.
Carrera, C.J., et al., "Potent Toxicity of 2-Chlorodeoxyadenosine Toward Human Monocytes in Vitro and in Vivo", J. Clin. Invest. 86:1480-1488, 1990.
Carson, D.A., et al., "Specific Toxicity of 2-Chlorodeoxyadenosine Toward Resting and Proliferating Human Lymphocytes", Blood 62: 737-743, 1983.
Chang, M.W., et al., Adenovirus-mediated Over-expression of the Cyclin/Cyclin-dependent Kinase Inhibitor, p. 21 J. Clin. Invest. 96: 2260-2268, 1995.
Circulation; 84: II-299 Abstracts From the 64th Scientific Sessions, 1991.

(Continued)

*Primary Examiner* — Bethany Barham

(57) ABSTRACT

Medical devices may be utilized for local and regional therapeutic agent delivery. These therapeutic agents or compounds may reduce a biological organism's reaction to the introduction of the medical device to the organism. In addition, these therapeutic drugs, agents and/or compounds may be utilized to promote healing, including the prevention of thrombosis. The drugs, agents, and/or compounds may also be utilized to treat specific disorders, including restenosis, vulnerable plaque, and atherosclerosis in type 2 diabetic patients.

11 Claims, 2 Drawing Sheets

U.S. PATENT DOCUMENTS

| | | | |
|---|---|---|---|
| 6,515,016 | B2 | 2/2003 | Hunter |
| 6,538,020 | B2 | 3/2003 | Joshi-Hangal et al. |
| 6,667,048 | B1 | 12/2003 | Lambert et al. |
| 6,753,006 | B1 | 6/2004 | Desai et al. |
| 6,764,507 | B2 | 7/2004 | Shanley et al. |
| 6,828,346 | B2 | 12/2004 | Joshi Hangal et al. |
| 6,919,370 | B2 | 7/2005 | Chen |
| 7,060,709 | B2 | 6/2006 | Cooperstone et al. |
| 2003/0083740 | A1* | 5/2003 | Pathak ..................... 623/1.43 |
| 2003/0087924 | A1 | 5/2003 | Sorenson |
| 2003/0105156 | A1 | 6/2003 | Palepu et al. |
| 2003/0170287 | A1 | 9/2003 | Prescott |
| 2003/0187062 | A1 | 10/2003 | Zenoni et al. |
| 2003/0204239 | A1 | 10/2003 | Carlyle et al. |
| 2003/0207936 | A1 | 11/2003 | Chen |
| 2004/0024003 | A1 | 2/2004 | Asmussen et al. |
| 2004/0106973 | A1 | 6/2004 | Johnson |
| 2004/0167152 | A1 | 8/2004 | Rubino et al. |
| 2004/0199241 | A1 | 10/2004 | Gravett et al. |
| 2004/0224003 | A1 | 11/2004 | Schultz |
| 2005/0222191 | A1 | 10/2005 | Falotico et al. |
| 2005/0244453 | A1* | 11/2005 | Stucke et al. ............. 424/423 |
| 2005/0249776 | A1 | 11/2005 | Chen et al. |
| 2005/0272806 | A1 | 12/2005 | Falotico et al. |
| 2006/0083768 | A1 | 4/2006 | Labrecque et al. |
| 2006/0188543 | A1 | 8/2006 | Feng |
| 2007/0202149 | A1 | 8/2007 | Faucher et al. |
| 2010/0233236 | A1 | 9/2010 | Zhao |
| 2010/0331816 | A1 | 12/2010 | Dadino et al. |

FOREIGN PATENT DOCUMENTS

| | | | |
|---|---|---|---|
| EP | 41795 | B1 | 1/1985 |
| EP | 590267 | B1 | 7/1993 |
| EP | 950386 | A | 10/1999 |
| WO | WO 93/10076 | A1 | 5/1993 |
| WO | WO 93/13555 | A1 | 8/1993 |
| WO | WO 93/19763 | A | 10/1993 |
| WO | WO 93/24476 | A1 | 12/1993 |
| WO | WO 94/00156 | A1 | 1/1994 |
| WO | WO 94/07876 | A1 | 4/1994 |
| WO | WO 94/07880 | A1 | 4/1994 |
| WO | WO 94/07881 | A1 | 4/1994 |
| WO | WO 94/07882 | A1 | 4/1994 |
| WO | WO 94/20089 | A1 | 9/1994 |
| WO | WO 98/33443 | A1 | 8/1998 |
| WO | WO9945918 | | 9/1999 |
| WO | WO0071163 | A1 | 11/2000 |
| WO | WO0130319 | A1 | 5/2001 |
| WO | WO0243765 | A2 | 6/2002 |
| WO | WO03057208 | A1 | 7/2003 |
| WO | WO2004002182 | A1 | 12/2003 |
| WO | WO 2004/011000 | A | 2/2004 |
| WO | WO 2004/026182 | | 4/2004 |
| WO | WO 2004/043510 | | 5/2004 |
| WO | WO2004091506 | A1 | 10/2004 |
| WO | WO 2004/110302 | | 12/2004 |

OTHER PUBLICATIONS

Clowes, A.W., et al., "Kinetics of Cellular Proliferation After Arterial Injury, II. Inhibition", Lab Invest 52(6):611-6, 1985.

Clowes, A.W., et al., "Kinetics of Cellular Proliferation After Arterial Injury, IV. Heparin", Circ Res 58:839-845, 1986.

Clowes, A.W., et al., "Suppression by Heparin of Smooth Muscle Cell Proliferation in Injured Arteries", Nature 265: 25-26, 1977.

Clowes and Schwartz, "Significance of Quiescent Smooth Muscle Migration in the Injured Rat Carotid Artery", Cir. Res. 56: 139-145 (1985).

Colburn, M.D. MD, et al., "Dose Responsive Suppression of Myointimal Hyperplasia by Dexamethasone", J. Vasc. Surg. 15:510-518, 1992.

Currier, J.W., et al., "Restenosis After Percutanous Transluminal Coronary Angioplasty: Have We Been Aiming at the Wrong Target?" JACC Vo. 25, No. 2, 516-20, Feb. 1995.

Currier, J.W., et al., "Colchicine Inhibits Restenosis After Iliac Angioplasty in the Atherosclerotic Rabbit", Circ. 80, No. 4, II-66, 1989.

Edelman, E., et al. "Pathobiologic Responses to Stenting", American Journal of Cardiology vol. 91, Issue 7, Suppl. 1, Sep. 1998.

Esterbauer, H. et al., "Continuous Monitoring of in Vitro Oxidation of Human Low Density Lipoprotein", Free Rad. Res. Comms., vol. 6, No. 1, 67-75, 1989.

Farb, A., et al., "Vascular Smooth Muscle Cell Cytotoxicity and Sustained Inhibition of Neointimal Formation by Fibroblast Growth Factor 2-Saporin Fusion Protein", Circ. Res., 80(4):542-50, 1997.

Ferns, G.A.A. et al., "Inhibition of Neointimal Smooth Muscle Accumulation After Angioplasty by an Antibody to PDGF", Science, vol. 253, Reports, 1129-1132, Sep. 6, 1991.

Ferns, G.A.A. et al., "Probucol Inhibits Neointimal Thickening and Macrophage Accumulation After Balloon Injury in the Cholesterol-Fed Rabbit", Proc. Natl. Acad. Sci. vol. 89, pp. 11312-11316, Dec. 1992.

Fischman, D., et al. "A Randomized Comparison of Coronary-Stent Placement and Balloon Angioplasty in the Treatment of Coronary Artery Disease", New England Journal of Medicine, vol. 331 (1994) pp. 496-501.

Fleischman, L., et al. "Ras-Transformed Cells: Altered Levels of Phosphatidylinositol-4,5-Bisphosphate and Catabolites", Reports Jan. 1986, p. 407.

Franke, T.F., et al., "PI3K:Downstream AKTion Blocks Apoptosis", Cell, vol. 88, 435-437, Feb. 21, 1997.

Fukuyama, J., et al., Tranilast Suppresses the Vascular Intimal Hyperplasia After Balloon Injury in Rabbits Fed on a High-Cholesterol Diet, Euro. Journal of Pharmacology, 318, 327-332, 1996.

Galis, Z.S., et al., "Cytokine-Stimulated Human Vascular Smooth Muscle Cells Synthesize a Complement of Enzymes Required for Extracellular Matrix Digestion", Circ. Res. 75:181-189, 1994.

Georg, G.I. et al., "Synthesis of Biologically Active Taxol Analogues with Modified Phenylisoserine Side Chains", J. Med. Chem. 35, 4230-4237, 1992.

Gimon, M.E. et al., "Matrix-Assisted Laser Desorption/Ionization Time-of-Flight Mass Spectrometry of Paclitaxel and Related Taxanes", Journal of Natural Products, vol. 57, No. 10, pp. 1404-1410, Oct. 1994.

Gueritte-Voegelein, F., et al., "Relationships Between the Structure of Taxol Analogues and Their Antimitotic Activity", J. Med. Chem. 34, 992-998, 1991.

Guyton, J.R., et al., "Inhibition of Rat Arterial Smooth Muscle Cell Proliferation by Heparin", Circulation Research, vol. 46, No. 5, 625-634, May 1980.

Haas-Kogan, D., et al., "Protein kinase B (PKB/Akt) Activity is Elevated in Glioblastoma Cells Due to Mutation of the Tumor Suppressor PTEN/MMAC", Current Biology, vol. 8, No. 21, 1195-1198 & S1, 1998.

Hansson, G. K., et al., "Interferon-Gamma Inhibits Arterial Stenosis After Injury", Circulation, 84; 1266-1272, 1991.

Hanson, S.R., et al., "Interruption of Acute Platelet-Dependent Thrombosis by the Synthetic Antithrombin D-phenylalanyl-L-prolyl-L-arginyl Chloromethyl Ketone", Proc. Natl. cad. Sci. vol. 85, 3184-3188, 1988.

Holton, R.A., et al., "A Synthesis of Taxusin", J. Am. Chem. Soc., vol. 110, No. 19, 6558-6560, 1988.

Ikada, Y., et al., "Sterocomplex Formulation Between Enantiomeric Poly(lactides)", Macromolecules, 20, 904-906, 1987.

Ku, G., "Inhibition by Probucol of Interleukin 1 Secretion and Its Implication in Atherosclerosis", Am J. Cardiol. 62:77B-81B, 1988.

Kugiyama, K., et al., "Impairment of Endothelium-Dependent Arterial Relaxation by Lysolecithin in Modified Low-Density Lipoproteins", Nature, 344(6262):160-2, 1990.

Kunishima, T. MD, et al., "A Randomized Trial of Aspirin Versus Cilostazol Therapy After Successful Coronary Stent Implantation", Clinical Therapeutics, vol. 19, No. 5, 1058-1066, 1997.

Kuzuya, M., et al., "Probucol Prevents Oxidative Injury to Endothelial Cells", Journal of Lipid Research, vol. 32, 197-204, 1991.

Lang, R. J., et al. "Effects of Okadaic Acid and ATYPγS on Cell Length and $Ca^{2+}$—Channel Currents Recorded in Single Smooth Muscle Cells of the Guinea-Pig Taenia Caeci", Br. J. Pharmacol. (1991) 104, p. 331-336.

Langille, B.L., et al., "Reductions in Arterial Diameter Produced by Chronic Decreases in Blood Flow Are Endothelium-Dependent", Reports, Science, vol. 231, 405-407, Jan. 1986.

Lee, Y.J. et al., "Effectiveness of Probucol in Preventing Restenosis After Percutaneous Transluminal Coronary Angioplasty", Jpn. Heart J. 327-332, May 1996.

Leibel S., et al. "Radiation Therapy for Neoplasms of the Brain", J. Neurosurgery vol. 66 (1987) p. 1-22.

Liu, M.W., et al., "Trapidil in Preventing Restenosis After Balloon Angioplasty in the Atherosclerotic Rabbit", Circulation 81, No. 3, 1089-1093, 1990.

Long, B.H., et. al., "Paclitaxel Inhibits Progression of Mitotic Cells to G Phase by Interference with Spindle Formation without Affecting Other Microtubule Functions during Anaphase and Telephase", Cancer Res. 54, 4355-4361, Aug. 15, 1994.

Lundergan, C.F., et al., "Peptide Inhibition of Myointimal Proliferation by Angiopeptin, a Somatostatin Analogue", JACC, vol. 17, No. 6, 132B-6B, May 1991.

Majesky, M.W., et al., "Heparin Regulates Smooth Muscle S Phase Entry in the Injured Rat Carotid Artery", Circ. Research, vol. 61, No. 2, 296-300, Aug. 1987.

Mak and Topol "Clinical Trials to Prevent Restenosis after Percutaneous Coronary Revascularization", Annals New York Academy of Sciences, p. 139-145 (1997).

Marx, S.O., et al., "Rapamycin-FKBP Inhibits Cell Cycle Regulators of Proliferation in Vascular Smooth Muscle Cells", Circ. Res., 76(3):412-7, 1995.

Mintz, G., et al., "Arterial Remodeling After Coronary Angioplasty: A Serial Intravascular Ultrasound Study", American Heart Association, Clinical Investigation and Reports, vol. 94(1), (1996) p. 35-43.

Morena, H., et al. "Comparison of the Effects of Regional Ischemia, Hypoxia, Hyperkalemia, an Acidosis on Intracellular and Extracellular Potentials and Metabolism in the Isolated Porcine Heart", Circulation Research, vol. 46, No. 5, May 1980 p. 634.

Nunes, G., "Combination of Vitamins C and E Alters the Response to Coronary Balloon Injury in the Pig", Arterioscler Thromb and Vasc Biol., 15(1):156-65, 1995.

Orgill, D. M.D. et al., "Current Concepts and Approaches to Wound Healing", Critical Care Medicine, vol. 16, No. 9, 899-908, Sep. 1988.

Ozaki, H., et al., "Calcium-Independent Phosphorylation of Smooth Muscle Myosin Light Chain by Okadiac Acid Isolated from Black Sponge", Journal of Pharmacology and Experimental Therapeutics, vol. 243, No. 3, 1167-1173, 1987.

Parthasarathy, S., et al., "Probucol Inhibits Oxidative Modification of Low Density Lipoprotein", J. Clin. Invest. vol. 77, 641-644, Feb. 1986.

Pazdur, R., et al., "The Taxoids: Paclitaxel (Taxol®) and Docetaxel (Taxotere®)", Cancer Treatment Reviews, 19, 351-386, 1993.

Pompa, J., et al. "Clinical Trials of Restenosis After Coronary Angioplasty", Circulation Journal of the American Heart Association, 84 p. 1426-1436 (1991).

Pozzati, E. MD, et al., "The Growth of Cerebral Cavernous Angiomas", Neurosurgery, vol. 25, No. 1, 92-97, 1989.

Powell, J.S., "Inhibitors of Angiotensin-Converting Enzyme Prevent Myointimal Proliferation After Vascular Injury", Science, vol. 245, 186-8, 1989.

Pulicani, J.-P., et al., "Preparation of 7-Modified Docetaxel Analogs Using Electrochemistry", Tetrahedron Letters, vol. 35, No. 52, pp. 9709-9712, 1994.

Rajagopalan, S., et al., "Reactive Oxygen Species Produced by Macrophage-derived Foam Cells Regulate the Activity of Vascular Matrix Metalloproteinases in Vitro", J. Clin. Invest., vol. 98, No. 11, 2572-2579, Dec. 1996.

Reiser, K., et al., Enzymatic and Nonenzymatic Cross-Linking of Collagen and Elastin, The FASEB Journal, vol. 6, 2439-2449, 1992.

Ringel, I, et al., "Studies With RP 56976 (Taxotere): A Semisynthetic Analogue of Taxol", J Nat'l Cancer Institute, 83(4):288-91, 1991.

Saito, N., et al. "Intramedullary Cavernous Angioma with Trigeminal Neuralgia: A Case Report and Review of the Literature", Neurosurgery (1989) p. 97.

Schiff, P.B., et al., "Promotion of Microtubule Assembly in vitro by Taxol", Nature, vol. 277, 665-667, Feb. 22, 1979.

Schneider, J.E., et al., "Probucol Decreases Neointimal Formation in a Swine Model of Coronary Artery Balloon Injury", Circulation 88:628-637, 1993.

Scully, R., et al. "Case Records of the Massachusetts General Hospital", The New England Journal of Medicine, (1989) p. 924.

Setsuda, M., et al. "Probucol Therapy in the Prevention of Restenosis After Successful Percutaneous Transluminal Coronary Angioplasty", Clinical Therapeutics, vol. 15, No. 2 (1993), p. 374.

Serruys, P.W., et al., "A Comparison of Balloon-Expandable-Stent Implantation With Balloon Angioplasty in Patients With Coronary Artery Disease", N Engl. J. Med., 331(8):489-95, 1994.

Shayesteh, L., et al. "PIK3CA is Implicated as an Oncogene in Ovarian Cancer", Nature Genetics, vol. 21 (1999) p. 99-102.

Siddiqui, J., et al., "Isolation and Sequencing of a cDNA Coding for the Human DF3 Breast Carcinoma-Associated Antigen", Proc. Nat. Acad. Sci., vol. 85, 2320-2323, Apr. 1998.

Simons, M., et al., "Antisense c-myb Oligonucleotides Inhibit lintimal Arterial Smooth Muscle Cell Accumulation in vivo", Nature, vol. 359, 67-70, Sep. 3, 1992.

Snow, A., et al. "Heparin Modulates the Composition of the Extracellular Matrix Domain Surrounding Arterial Smooth Muscle Cells", American Journal of Pathology, vol. 73, No. 2, (1990), p. 313.

Sollott, S , et al., "Taxol Inhibits Neointimal Smooth Muscle Cell Accumulation After Angioplasty in the Rat", The Journal of Clinical Investigation, Inc., vol. 95, 1869-1876, Apr. 1995.

Southgate, K.M., et al., "Involvement of Extracellular-matrix-degrading Metalloproteinases in Rabbit Aortic Smooth-Muscle Cell Proliferation", Biochem J, 288:93-99, 1992.

Southorn, P.A., et al., "Free Radicals in Medicine. I. Chemical Nature and Biologic Reactions", Mayo Clin Proc. 63:381-389, 1988.

Steinberg, D., et. al., "Beyond Cholesterol. Modifications of Low-Density Lipoprotein That Increase Its Atherogenicity", vol. 320. No. 14, 915-924 1989.

Steinberg, D., Studies on the Mechanism of Action of Probucol, Am J. Cardiol, 57:16H-21H, 1986.

Stierle, A., et al., "Taxol and Taxane Production by Taxomyces andreanae, an Endophytic Fungus of Pacific Yew", Science, vol. 260, 214-216, Apr. 9, 1993.

Strauss, B., et al., "Extracellular Matrix Remodeling After Balloon Angioplasty Injury in a Rabbit Model of Restenosis", Circ Res 75:650-658, 1994.

Take, S., et al., "Effect of Cilostazol in Preventing Restenosis After Percutaneous Transluminal Coronary Anioplasty", Am J. of Cardiology, vol. 79, 1097-1099, 1997.

Tanaka, H., et al. "Sustained Activation of Vascular Cells and Leukocytes in the Rabbit Aorta after Balloon Injury", Circulation vol. 88 p. 1788 (19930, 1993.

Tardif, J.-C., et al., "Probucol and Multivitamins in the Prevention of Restenosis After Coronary Angioplasty", New Eng. J. Medicine, vol. 337, No. 6, 365-372, Aug. 7, 1997.

Tsuchikane, E., et al., "Impact of Cilostazol on Restenosis After Percutaneous Coronary Balloon Angioplasty", Circulation, 21-26, Jul 6, 1999.

Watanabe, K., et al., "Preventive Effects of Probucol on Restenosis After Percutaneous Transluminal Coronary Angioplasty", Am. Heart Journal, vol. 132, No. 1, Part 1., 23-29, Jul. 1996.

Weinberger, J, M.D., et al., "Intracoronary Irradiation: Dose Response for the Prevention of Restenosis in Swine", Int. J. Radiation Oncology Biol. Phys. vol. 36, No. 4, 767-775, 1996.

Yokoi, H., "Effectiveness of an Antioxidant in Preventing Restenosis After Percutaneous Transluminal Coronary Angioplasty: The Probucol Angioplasty Restenosis Trial", JACC. vol. 30., No. 4, 855-62, Oct. 1997.

Zhang, S., et al. "*A New 11(15/1)-Abeo-Taxane from Taxus Yunnanensis*", Journal of Natural Products, vol. 57, No. 11, 1580-1583, Nov. 1994.

European Search Report dated Aug. 2, 2007 for corresponding Application No. 05252016.0-1219.

U.S. Appl. No. 09/948,987, See US Patent 6,764,507.

Beutler, E., "Cladribine (2-chlorodeoxyadenosine)", The Lancet, vol. 340, pp. 952-956 (Oct. 1992).

Brehm, B., et al. "β-Blockers of the Third Generation Inhibit Endothelin-1-Liberation, mRNA Production and Proliferation of Human Coronary Smooth Muscle and Endothelial Cells", Journal of Cardiovascular Pharmacology, (2000) Suppl. 1, vol. 36, pp. S401-S403.

Burton, G., et al. "β-Carotene: An Unusual Type of Lipid Antioxidant", Science, vol. 224 (1984) pp. 569-573.

Campbell & Campbell, "Phenotypic Modulation of Smooth Muscle Cells in Primary Culture" (Table of Contents), Chapter 4, vol. 1, pp. 39-52 (1985).

Deroanne, C., et al. "Histone Deacetylases Inhibitors as Anti-Angiogenic Agents Altering Vascular Endothelial Growth Factor Signaling", Oncogene (2002) vol. 21, pp. 427-436.

Edelman, E., et al. "Pathobiologic Responses to Stenting", American Journal of Cardiology, vol. 81, Issue 7, Suppl. 1 (Apr. 1998) pp. 4E-6E.

Franklin, S., et al. "Pharmacologic Prevention of Restenosis After Coronary Angioplasty: Review of the Randomized Clinical Trials", Coronary Artery Disease, vol. 4, No. 3 (Mar. 1993) pp. 232-242.

Jonasson, L., et al. "Cyclosporin A Inhibitors Smooth Muscle Proliferation in the Vascular Response to Injury", Proc. Natl. Acad. Sci (USA) vol. 85 (Apr. 1988) pp. 2303-2306.

Mak and Topol, K., et al. "Clinical Trials to Prevent Restenosis After Percutaneous Coronary Revascularization", Department of Cardiolg. Cleveland Clinical Foundation, Ohio pp. 255-288 (1991).

Nemecek, G., et al. "Terbinafine Inhibits the Mitogenic Response to Plalet-Derived Growth Factor in Vitro and Neotintimal Proliferation in Vivo", Journal of Pharmacology and Experimental Therapeutics, vol. 245(3) pp. 1167-1174, 1989.

Okada, T., et al. "Localized Release of Perivascular Heparian Inhibits Intimal Proliferation After Endothelial Injury Without Systemic Anticoagulation", Neurosurgery(1989), vol. 25(6), pp. 892-898.

Serruys, P., et al. "Heparin-Coated Palmaz-Schartz Stents in Human Coronary Arteries Early Outcome of the Benestent-II Pilot Study", Circulation, vol. 93(3) (Feb. 1996) pp. 412-422.

Serruys, P., et al. "Evaluation of Ketanserin in the Prevention of Restenosis After Percutaneous Transluminal Coronary Angioplasty. A Multicenter Randomized Double-Blind Placebo-Controlled Trial", American Heart Association, Circulation 88 (1993) pp. 1588-1601.

Tanaka, H., et al., "Sustained Activation of Vascular Cells and Leukocytes in the Rabbit Aorta After Balloon Injury", Circulation, vol. 88, pp. 1788-1803 (1993).

Teirstein, P., et al. "Catheter-Based Radiotherapy to Inhibit Restenosis After Coronary Stenting", vol. 336, No. 24 (Jun. 1997) p. 1679.

Wiley and Sons, Chapter 2: "Modern Fluoropolymers—High Performance Polymers for Diverse Applications", pp. 71-90 (1997).

Woo, S., et al. Structurally Simple Trichostatin A-Like Straight Chain Hydroxamates as Potent Histone Deacetylase Inhibitors, J. Med. Chemistry (2002) vol. 45, pp. 2877-2885.

Arcella, V., et al., "Modern Fluoropolymers-High Performance Polymers for Diverse Applications," Wiley Series in Polymer Science, John Wiley & Sons Ltd., 1997, pp. 77-87, New York NY.

Brehm, B. R., et al, "Chronically Elevated Endothelin-1 Concentrations Modulate the B-Adrenergic Receptor System in Vitro and in Vivo" Journal of Cardiovascular Pharmacology, 2000, pp. S157-S159, London.

Campbell, G. R., et al., "Recent Advances in Molecular Pathology," Department of Anatomy, University of Melbourne, Jul. 3,1984, pp. 139-162, Australia.

Carson, D. A., et al., "Genetic Analysis of Deoxyadenosine Toxicity in Dividing Human Lymphoblasts," Department of Basic and Clinical Research Scripps Clinic and Research Foundation, La Jolla, California, pp. 207-211. Adv. Exp. Med. Biol.; 195 Pt.B (1986).

Carson, D. A., et al., "DNA Strand Breaks, NAD Metabolism, and Programmed Cell Death," Department of Basic and Clinical Research Scripps Clinic and Research Foundation, 1986, La Jolla, California, pp. 273-281.

Carson, D. A., et al., "Metabolism to Methionine and Growth Stimulation by 5'-Methylthioadenosine and 5'-Methylthioinosine in Mammalian Cells," Biochemical and Biophysical Research Communications, Department of Basic and Clinical Research Scripps Clinic and Research Foundation, Apr. 29, 1983, La Jolla, California, pp. 391-397, vol. 112, No. 2.

Carson, D. A., et al., "Lymphocyte Dysfunction after DNA damage by toxic oxygen species. A Model of Immunodeficiency," The Rockefeller University Press, Mar. 1, 1986, pp. 746-751, vol. 163, No. 3.

Clowes, A. W., et al., "Significance of Quiescent Smooth Muscle Migration in the Injured Rat Carotid Artery," Circulation Research, Jan. 1985, pp. 139-145, vol. 56, No. 1.

Fleiss, J. L., "The Design and Analysis of Clinical Experiments," Wiley Classics Library Edition, 1986.

"Sirolimus," Wikipedia, the free encyclopedia, pp. 1-2. (retrieved online on Aug. 30, 2010).

Keane, D., et al., "Clinical and angiographic outcome of elective stent implantation in small coronary vessels: an analysis of the Benestent trial," Semin Intervent Cardiol, 1996, pp. 255-262, vol. 1.

Lang, R. J., et al., Effects of okadaic acid and ATPγS on cell length and Ca2+-channel currents recorded in single smooth muscle cells of the guinea-pig taenia caeci, Br. J. Pharmacol, 1991, Australia, pp. 331-336, vol. 104.

Lang, R. J., et al., "Effects of 2,3-Butanedione Monoxime on Whole-Cell Ca2+ Channel Currents in Single Cells of the Guinea-Pig Taenia Caeci," Journal of Physiology, Mar. 13, 1990, Great Britain, vol. 433, pp. 1-24.

Liang, K-Y, "Longitudinal data analysis using generalized linear models," Biomedtrika, Oct. 1985, Great Britain, pp. 13-22, vol. 73.

Lifu, M., et al., "Advances in Treatment of Coronary Restenosis Using Rapamycin," Journal of Clinical Cardiology, Sep. 2003, vol. 19, No. 9.

Mintz, G. S., et al., "Intravascular Ultrasound Findings After Excimer Laser Coronary Angioplasty," Catheterization and Cardiovascular Diagnosis, 1996, pp. 113-118, vol. 37.

Mintz, G. S., et al., "Intravascular Ultrasound Assessment of the Mechanisms and Predictors of Restenosis Following Coronary Angioplasty," Intravascular Ultrasound Imaging and Cardiac Catheterization Laboratory of the Washington Hospital Center, Washington D.C., Jan./Feb. 1996, pp. 1-14, vol. 8, No. 1.

Mintz, G. S., et al., "Intravascular Ultrasound to Discern Device-Specific Effects and Mechanisms of Restenosis," American Journal of Cardiology, 1996, pp. 18-22, vol. 78 (Suppl 3A).

Mintz, G. S., et al., "Determinants and Correlates of Target Lesion Calcium in Coronary Artery Disease: A Clinical, Angiographic and Intravascular Ultrasound Study," Coronary Artery Disease, Journal of the American College Cardiology, 1997, pp. 268-274, vol. 29.

Mintz, G. S., et al., "Axial Plaque Redistribution as a Mechanism of Percutaneous Transluminal Coronary Angioplasty," Intravascular Ultrasound Imaging and Cardiac Catheterization Laboratory of the Washington Hospital Center Brief Reports, Oct. 17, 1995, pp. 427-430.

Nemecek, G. M., et al., "Terbinafine Inhibits the Mitogenic Response to Platelet-Derived Growth Factor in Vitro and Neointimal Proliferation in Vivo," The Journal of Pharmacology and Experimental Therapeutics, 1989, pp. 1167-1174, vol. 248, No. 3.

Kuzuya, M., et al, "Probucol prevents oxidative injury to endothelial cells," Journal of Lipid Research,1991, pp. 197-204, vol. 32.

Popma, J. J., et al., "Clinical, Angiographic and Procedural Correlates of Quantitative Coronary Dimensions After Directional Coronary Atherectomy," Journal of the American College Cardiology, 1991, pp. 1183-1189, vol. 18.

Popma, J. J., et al., "Adjuncts to Thrombolysis for Myocardial Reperfusion," Annals of Internal Medicine, 1991, pp. 34-44. vol. 115.

Popma, J. J., et al., "Atherectomy of Right Coronary Ostial Stenoses: Initial and Long-Term Results, Technical Features and Histologic Findings," The American Journal of Cardiology, Feb. 15, 1991, pp. 431-433 vol. 67.

Serruys, P. W., et al., "The Bailout Stent, Is a Friend in Need Always a Friend Indeed?" Nov. 1993, Circulation, pp. 2455-2457, vol. 88, No. 5, Part 1.

Seto, S., et al., "Mechanism of Deoxyadenosine and 2-Chlorodeoxyadenosine Toxicity to Nondividing Human Lymphocytes," Journal of Clinical Investigation, Feb. 1985, pp. 377-383, vol. 75.

Tardif, J. C., et al., "Probucol and Multivitamins in the Prevention of Restenosis after Coronary Angioplasty," The New England Journal of Medicine, Aug. 7, 1997, pp. 627-633, vol. 337.

Yang, J., et al., "Coated Stents in Blood Vessel," Advances in Cardiovascular Diseases, 2002, vol. 23, No. 6.

Serruys, P. W., et al, "Randomized Trials of Coronary Stenting," Journal of Interventional Cardiology, 1994, p. 331, vol. 7, No. 4.

Serruys, P. W., et al, "Heparin-Coated Palmaz-Schatz Stents in Human Coronary Arteries: Early Outcome of the Benestent-II Pilot Study," 1996, Circulation, pp. 412-422, vol. 93.

Mintz, G. S., et al., "Intravascular Ultrasound Predictors of Restenosis After Percutaneous Transcatheter Coronary Revascularization," Journal of the American College Cardiology, 1996, pp. 1678-1687, vol. 27, No. 7.

Mintz, G. S., et al., "Limitations of Angiography in the Assessment of Plaque Distribution in Coronary Artery Disease, A Systematic Study of Target Lesion Eccentricity in 1446 Lesions," Circulation, 1996, pp. 924-932, No. 93.

Extended European Search Report and Written Opinion dated Nov. 29, 2012 for corresponding EP Patent Application No. EP09250946.

* cited by examiner 200
202
204

206

DRUG COATED EXPANDABLE DEVICES

CROSS REFERENCE TO RELATED APPLICATIONS

This application is a continuation-in-part of U.S. patent application Ser. No. 12/059,291 filed Mar. 31, 2008 now U.S. Pat. No. 8,003,122.

BACKGROUND OF THE INVENTION

1. Field of the Invention

The present invention relates to the local and/or regional administration of therapeutic agents and/or therapeutic agent combinations, and more particularly to expandable medical devices for the local and/or regional delivery of therapeutic agents and/or therapeutic agent combinations for the prevention and treatment of vascular disease.

2. Discussion of the Related Art

Many individuals suffer from circulatory disease caused by a progressive blockage of the blood vessels that perfuse the heart and other major organs. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel, which may occur immediately after the procedure and restenosis, which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

Upon pressure expansion of an intracoronary balloon catheter during angioplasty and/or stent implantation, smooth muscle cells and endothelial cells within the vessel wall become injured, initiating a thrombotic and inflammatory response. Cell derived growth factors such as platelet derived growth factor, basic fibroblast growth factor, epidermal growth factor, thrombin, etc., released from platelets, invading macrophages and/or leukocytes, or directly from the smooth muscle cells provoke a proliferative and migratory response in medial smooth muscle cells. These cells undergo a change from a contractile phenotype to a synthetic phenotype characterized by only a few contractile filament bundles, extensive rough endoplasmic reticulum, Golgi and free ribosomes. Proliferation/migration usually begins within one to two days' post-injury and peaks several days thereafter (Campbell and Campbell, 1987; Clowes and Schwartz, 1985).

Daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells adhere to the site of vascular injury. Within three to seven days post-injury, inflammatory cells have migrated to the deeper layers of the vessel wall. In animal models employing either balloon injury or stent implantation, inflammatory cells may persist at the site of vascular injury for at least thirty days (Tanaka et al., 1993; Edelman et al., 1998). Inflammatory cells therefore are present and may contribute to both the acute and chronic phases of restenosis.

Unlike systemic pharmacologic therapy, stents have proven useful in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994).

Additionally, the heparin coating of stents appears to have the added benefit of producing a reduction in sub-acute thrombosis after stent implantation (Serruys et al., 1996). Thus, sustained mechanical expansion of a stenosed coronary artery with a stent has been shown to provide some measure of restenosis prevention, and the coating of stents with heparin has demonstrated both the feasibility and the clinical usefulness of delivering drugs locally, at the site of injured tissue. However, in certain circumstances it may not be desirable to leave any type of implantable device in the body.

Accordingly, there exists a need for drug/drug combinations and associated local delivery devices for the prevention and treatment of vascular injury causing intimal thickening which is either biologically induced, for example, atherosclerosis, or mechanically induced, for example, through percutaneous transluminal coronary angioplasty.

SUMMARY OF THE INVENTION

A device for local and/or regional delivery employing liquid formulations of therapeutic agents in accordance with the present invention may be utilized to overcome the disadvantages set forth above.

Medical devices may be utilized for local and regional therapeutic agent delivery. These therapeutic agents or compounds may reduce a biological organism's reaction to the introduction of the medical device to the organism. In addition, these therapeutic drugs, agents and/or compounds may be utilized to promote healing, including the prevention of thrombosis. The drugs, agents, and/or compounds may also be utilized to treat specific disorders, including restenosis, vulnerable plaque, and atherosclerosis in type 2 diabetic patients.

The drugs, agents or compounds will vary depending upon the type of medical device, the reaction to the introduction of the medical device and/or the disease sought to be treated.

The type of coating or vehicle utilized to immobilize the drugs, agents or compounds to the medical device may also vary depending on a number of factors, including the type of medical device, the type of drug, agent or compound and the rate of release thereof.

The present invention is directed to balloons or other inflatable or expandable devices that may be temporarily positioned within a body to deliver a therapeutic agent and/or continuation of therapeutic agents and then removed. The therapeutic agents may include liquid formulations of rapamycin. This type of delivery device may be particularly advantageous in the vasculature where stents may not be suitable, for example, in the larger vessels of the peripheral vascular system.

In use, the balloon or other inflatable or expandable device may be coated with one or more liquid formulations of therapeutic agent(s) and delivered to a treatment site. The act of inflation or expansion would, force the therapeutic agents into the surrounding tissue. The device may be kept in position for a period of between ten seconds to about five minutes depending upon the location. If utilized in the heart, shorter durations are required relative to other areas such as the leg.

In accordance with a first aspect, the present invention is directed to a medical device comprising expandable member having a first diameter for insertion into a vessel and a second diameter for making contact with the vessel walls, and a liquid formulation of a rapamycin affixed to at least a portion of the surface of the expandable member, the liquid formulation of a rapamycin comprising about 50 mg/ml of a rapamycin, about 5 mg/ml of a first excipient selected from the group of polymers consisting of PEG 400, PEG 1000, PEG 1500, PEG 2000 and polyvinyl alcohol, about 5 mg/ml of a second excipient selected from the group of antioxidants consisting of BHT, BHA and vitamin E TPGS, ascorbyl palmitate, resveratrol, and acetone and water in a ratio of about 60/40 to about 75/25.

In accordance with another aspect, the present invention is directed to a method for coating a device comprising making a liquid formulation of a rapamycin comprising about 50 mg/ml of a rapamycin, about 5 mg/ml of a first excipient selected from the group of polymers consisting of PEG 400, PEG 100, PEG 1500, PEG 2000 and polyvinyl alcohol, about 5 mg/ml of a second excipient selected from the group of antioxidants consisting of BHT, BHA and vitamin E TPGS, ascorbyl palmitate, resveratrol, and acetone and water in a ratio of about 60/40 to about 75/25, coating an expandable device with the liquid formulation for less than 10 seconds, drying the coated expandable device for about 10 minutes, recoating the expandable device with the liquid formulation for less than 5 seconds, and drying the recoated expandable device for about 10 minutes.

In accordance with yet another aspect, the present invention is directed to a liquid formulation of a rapamycin comprising about 50 mg/ml of a rapamycin, about 50 mg/ml of a first excipient selected from the group of polymers consisting of PEG 400, PEG 1000, PEG 1500, PEG 2000 and polyvinyl alcohol, about 5 mg/ml of a second excipient selected from the group of antioxidants consisting of BHT, BHA and vitamin E TPGS, ascorbyl palmitate, resveratrol, and acetone and water in a ratio of about 60/40 to about 75/25.

In accordance with still another aspect, the present invention is directed to method for the treatment of vascular disease comprising positioning an expandable member having a first unexpanded diameter proximate a treatment site of a diseased vessel, and expanding the expandable member to a second diameter such that it makes contact with the vessel walls at the treatment site, the expandable member having a coating comprising about 50 mg/ml of a rapamycin, about 5 mg/ml of a first excipient selected from the group of polymers consisting of PEG 400, PEG 100, PEG 1500, PEG 2000 and polyvinyl alcohol, about 5 mg/ml of a second excipient selected from the group of antioxidants consisting of BHT, BHA and vitamin E TPGS, ascorbyl palmitate, resveratrol, and acetone and water in a ratio of about 60/40 to about 75/25, wherein the expansion of the expandable member to its second diameter facilitates the uptake of the liquid formulation into the tissues comprising the vessel walls.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
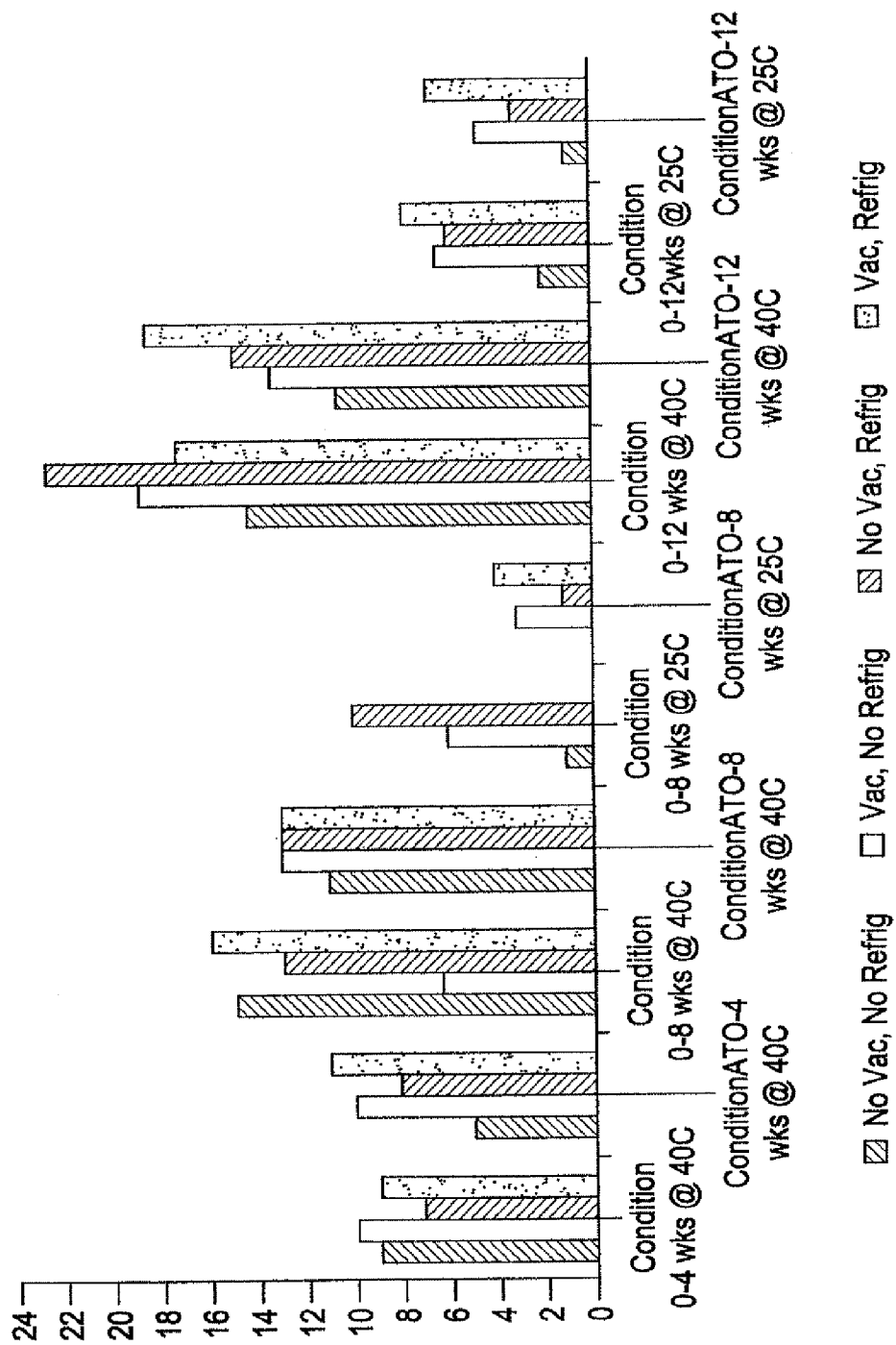
FIG. 1 is a graphical representation of the results of a bioactivity study in accordance with the present invention.

The drug/drug combinations and delivery devices of the present invention may be utilized to effectively prevent and treat vascular disease, including vascular disease caused by injury. Various medical treatment devices utilized in the treatment of vascular disease may ultimately induce further complications. For example, balloon angioplasty is a procedure utilized to increase blood flow through an artery and is the predominant treatment for coronary vessel stenosis. However, the procedure typically causes a certain degree of damage to the vessel wall, thereby potentially exacerbating the problem at a point later in time. Although other procedures and diseases may cause similar injury, exemplary embodiments of the present invention will be described with respect to the treatment of restenosis and related complications.

While exemplary embodiments of the invention will be described with respect to the treatment of restenosis and related complications following percutaneous transluminal coronary angioplasty, it is important to note that the local delivery of drug/drug combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any type of medical device may be coated in some fashion with a drug or drug combination which enhances treatment over use of the singular use of the device or pharmaceutical agent.

In addition to various medical devices, the coatings on these devices may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodolac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Rapamycin is a macrocyclic triene antibiotic produced by *Streptomyces hygroscopicus* as disclosed in U.S. Pat. No. 3,929,992. It has been found that rapamycin among other things inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin reduces vascular hyperplasia by antagonizing smooth muscle proliferation in response to mitogenic signals that are released during an angioplasty induced injury. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppressive activity and its ability to prevent graft rejection.

The molecular events that are responsible for the actions of rapamycin, a known anti-proliferative, which acts to reduce the magnitude and duration of neointimal hyperplasia, are still being elucidated. It is known, however, that rapamycin enters cells and binds to a high-affinity cytosolic protein called FKBP12. The complex of rapamycin and FKPB12 in turn binds to and inhibits a phosphoinositide (PI)-3 kinase called the "mammalian Target of Rapamycin" or TOR. TOR is a protein kinase that plays a key role in mediating the downstream signaling events associated with mitogenic growth factors and cytokines in smooth muscle cells and T lymphocytes. These events include phosphorylation of p27, phosphorylation of p70 s6 kinase and phosphorylation of 4BP-1, an important regulator of protein translation.

It is recognized that rapamycin reduces restenosis by inhibiting neointimal hyperplasia. However, there is evidence that rapamycin may also inhibit the other major component of restenosis, namely, negative remodeling. Remodeling is a process whose mechanism is not clearly understood but which results in shrinkage of the external elastic lamina and reduction in lumenal area over time, generally a period of approximately three to six months in humans.

Negative or constrictive vascular remodeling may be quantified angiographically as the percent diameter stenosis at the lesion site where there is no stent to obstruct the process. If late lumen loss is abolished in-lesion, it may be inferred that negative remodeling has been inhibited. Another method of determining the degree of remodeling involves measuring in-lesion external elastic lamina area using intravascular ultrasound (IVUS). Intravascular ultrasound is a technique that can image the external elastic lamina as well as the vascular lumen. Changes in the external elastic lamina proximal and distal to the stent from the post-procedural timepoint to four-month and twelve-month follow-ups are reflective of remodeling changes.

Evidence that rapamycin exerts an effect on remodeling comes from human implant studies with rapamycin coated stents showing a very low degree of restenosis in-lesion as well as in-stent. In-lesion parameters are usually measured approximately five millimeters on either side of the stent i.e. proximal and distal. Since the stent is not present to control remodeling in these zones which are still affected by balloon expansion, it may be inferred that rapamycin is preventing vascular remodeling.

The local delivery of drug/drug combinations from a stent has the following advantages; namely, the prevention of vessel recoil and remodeling through the scaffolding action of the stent and the prevention of multiple components of neointimal hyperplasia or restenosis as well as a reduction in inflammation and thrombosis. This local administration of drugs, agents or compounds to stented coronary arteries may also have additional therapeutic benefit. For example, higher tissue concentrations of the drugs, agents or compounds may be achieved utilizing local delivery, rather than systemic administration. In addition, reduced systemic toxicity may be achieved utilizing local delivery rather than systemic administration while maintaining higher tissue concentrations. Also in utilizing local delivery from a stent rather than systemic administration, a single procedure may suffice with better patient compliance. An additional benefit of combination drug, agent, and/or compound therapy may be to reduce the dose of each of the therapeutic drugs, agents or compounds, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, anti-thrombotic drugs, agents or compounds.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

The data in Table 1 below illustrate that in-lesion percent diameter stenosis remains low in the rapamycin treated groups, even at twelve months. Accordingly, these results support the hypothesis that rapamycin reduces remodeling.

TABLE 1.0

Angiographic In-Lesion Percent Diameter Stenosis (%, mean ± SD and "n=") In Patients Who Received a Rapamycin-Coated Stent

| Coating Group | Post Placement | 4-6 month Follow Up | 12 month Follow Up |
|---|---|---|---|
| Brazil | 10.6 ± 5.7 (30) | 13.6 ± 8.6 (30) | 22.3 ± 7.2 (15) |
| Netherlands | 14.7 ± 8.8 | 22.4 ± 6.4 | — |

Additional evidence supporting a reduction in negative remodeling with rapamycin comes from intravascular ultrasound data that was obtained from a first-in-man clinical program as illustrated in Table 2 below.

TABLE 2.0

Matched IVUS data in Patients Who Received a Rapamycin-Coated Stent

| IVUS Parameter | Post (n=) | 4-Month Follow-Up (n=) | 12-Month Follow-Up (n=) |
|---|---|---|---|
| Mean proximal vessel area (mm$^2$) | 16.53 ± 3.53 (27) | 16.31 ± 4.36 (28) | 13.96 ± 2.26 (13) |
| Mean distal vessel area (mm$^2$) | 13.12 ± 3.68 (26) | 13.53 ± 4.17 (26) | 12.49 ± 3.25 (14) |

The data illustrated that there is minimal loss of vessel area proximally or distally which indicates that inhibition of negative remodeling has occurred in vessels treated with rapamycin-coated stents.

Other than the stent itself, there have been no effective solutions to the problem of vascular remodeling. Accordingly, rapamycin may represent a biological approach to controlling the vascular remodeling phenomenon.

It may be hypothesized that rapamycin acts to reduce negative remodeling in several ways. By specifically blocking the proliferation of fibroblasts in the vascular wall in response to injury, rapamycin may reduce the formation of vascular scar tissue. Rapamycin may also affect the translation of key proteins involved in collagen formation or metabolism.

In an exemplary embodiment, the rapamycin is delivered by a local delivery device to control negative remodeling of an arterial segment after balloon angioplasty as a means of reducing or preventing restenosis. While any delivery device may be utilized, it is preferred that the delivery device comprises a stent that includes a coating or sheath which elutes or releases rapamycin. The delivery system for such a device may comprise a local infusion catheter that delivers rapamycin at a rate controlled by the administrator.

Rapamycin may also be delivered systemically using an oral dosage form or a chronic injectible depot form or a patch to deliver rapamycin for a period ranging from about seven to forty-five days to achieve vascular tissue levels that are sufficient to inhibit negative remodeling. Such treatment is to be used to reduce or prevent restenosis when administered several days prior to elective angioplasty with or without a stent.

Data generated in porcine and rabbit models show that the release of rapamycin into the vascular wall from a nonerodible polymeric stent coating in a range of doses (35-430 ug/15-18 mm coronary stent) produces a peak fifty to fifty-five percent reduction in neointimal hyperplasia as set forth in Table 3 below. This reduction, which is maximal at about twenty-eight to thirty days, is typically not sustained in the range of ninety to one hundred eighty days in the porcine model as set forth in Table 4 below.

TABLE 3.0

Animal Studies with Rapamycin-coated stents.
Values are mean ± Standard Error of Mean

| Study | Duration | Stent[1] | Rapamycin | N | Neointimal Area (mm²) | % Change From Polyme | % Change From Metal |
|---|---|---|---|---|---|---|---|
| Porcine | | | | | | | |
| 98009 | 14 days | Metal | | 8 | 2.04 ± 0.17 | | |
| | | 1X + rapamycin | 153 μg | 8 | 1.66 ± 0.17* | −42% | −19% |
| | | 1X + TC300 + rapamycin | 155 μg | 8 | 1.51 ± 0.19* | −47% | −26% |
| 99005 | 28 days | Metal | | 10 | 2.29 ± 0.21 | | |
| | | | | 9 | 3.91 ± 0.60** | | |
| | | 1X + TC30 + rapamycin | 130 μg | 8 | 2.81 ± 0.34 | | +23% |
| | | 1X + TC100 + rapamycin | 120 μg | 9 | 2.62 ± 0.21 | | +14% |
| 99006 | 28 days | Metal | | 12 | 4.57 ± 0.46 | | |
| | | EVA/BMA 3X | | 12 | 5.02 ± 0.62 | | +10% |
| | | 1X + rapamycin | 125 μg | 11 | 2.84 ± 0.31* ** | −43% | −38% |
| | | 3X + rapamycin | 430 μg | 12 | 3.06 ± 0.17* ** | −39% | −33% |
| | | 3X + rapamycin | 157 μg | 12 | 2.77 ± 0.41* ** | −45% | −39% |
| 99011 | 28 days | Metal | | 11 | 3.09 ± 0.27 | | |
| | | | | 11 | 4.52 ± 0.37 | | |
| | | 1X + rapamycin | 189 μg | 14 | 3.05 ± 0.35 | | −1% |
| | | 3X + rapamycin/dex | 182/363 μg | 14 | 2.72 ± 0.71 | | −12% |
| 99021 | 60 days | Metal | | 12 | 2.14 ± 0.25 | | |
| | | 1X + rapamycin | 181 μg | 12 | 2.95 ± 0.38 | | +38% |
| 99034 | 28 days | Metal | | 8 | 5.24 ± 0.58 | | |
| | | 1X + rapamycin | 186 μg | 8 | 2.47 ± 0.33** | | −53% |
| | | 3X + rapamycin/dex | 185/369 μg | 6 | 2.42 ± 0.64** | | −54% |
| 20001 | 28 days | Metal | | 6 | 1.81 ± 0.09 | | |
| | | 1X + rapamycin | 172 μg | 5 | 1.66 ± 0.44 | | −8% |
| 20007 | 30 days | Metal | | 9 | 2.94 ± 0.43 | | |
| | | 1XTC + rapamycin | 155 μg | 10 | 1.40 ± 0.11* | | −52%* |
| Rabbit | | | | | | | |
| 99019 | 28 days | Metal | | 8 | 1.20 ± 0.07 | | |
| | | EVA/BMA 1X | | 10 | 1.26 ± 0.16 | | +5% |
| | | 1X + rapamycin | 64 μg | 9 | 0.92 ± 0.14 | −27% | −23% |
| | | 1X + rapamycin | 196 μg | 10 | 0.66 ± 0.12* ** | −48% | −45% |
| 99020 | 28 days | Metal | | 12 | 1.18 ± 0.10 | | |
| | | EVA/BMA 1X + rapamycin | 197 μg | 8 | 0.81 ± 0.16 | | −32% |

[1]Stent nomenclature: EVA/BMA 1X, 2X, and 3X signifies approx. 500 μg, 1000 μg, and 1500 μg total mass (polymer + drug), respectively. TC, top coat of 30 μg, 100 μg, or 300 μg drug-free BMA; Biphasic; 2 × 1X layers of rapamycin in EVA/BMA spearated by a 100 μg drug-free BMA layer.
[2]0.25 mg/kg/d × 14 d preceeded by a loading dose of 0.5 mg/kg/d × 3 d prior to stent implantation.
*p < 0.05 from EVA/BMA control.
** p < 0.05 from Metal;
Inflammation score: (0 = essentially no intimal involvement; 1 = <25% intima involved; 2 = ≧25% intima involved; 3 = >50% intima involved).

TABLE 4.0

180 day Porcine Study with Rapamycin-coated stents.
Values are mean ± Standard Error of Mean

| Study | Duration | Stent[1] | Rapamycin | N | Neointimal Area (mm²) | % Change From Polyme | % Change From Metal | Inflammation Score # |
|---|---|---|---|---|---|---|---|---|
| 20007 | 3 days | Metal | | 10 | 0.38 ± 0.06 | | | 1.05 ± 0.06 |
| (ETP-2-002233-P) | | 1XTC + rapamycin | 155 μg | 10 | 0.29 ± 0.03 | | −24% | 1.08 ± 0.04 |
| | 30 days | Metal | | 9 | 2.94 ± 0.43 | | | 0.11 ± 0.08 |
| | | 1XTC + rapamycin | 155 μg | 10 | 1.40 ± 0.11* | | −52%* | 0.25 ± 0.10 |
| | 90 days | Metal | | 10 | 3.45 ± 0.34 | | | 0.20 ± 0.08 |
| | | 1XTC + rapamycin | 155 μg | 10 | 3.03 ± 0.29 | | −12% | 0.80 ± 0.23 |
| | | 1X + rapamycin | 171 μg | 10 | 2.86 ± 0.35 | | −17% | 0.60 ± 0.23 |
| | 180 days | Metal | | 10 | 3.65 ± 0.39 | | | 0.65 ± 0.21 |
| | | 1XTC + rapamycin | 155 μg | 10 | 3.34 ± 0.31 | | −8% | 1.50 ± 0.34 |
| | | 1X + rapamycin | 171 μg | 10 | 3.87 ± 0.28 | | +6% | 1.68 ± 0.37 |

The release of rapamycin into the vascular wall of a human from a nonerodible polymeric stent coating provides superior results with respect to the magnitude and duration of the reduction in neointimal hyperplasia within the stent as compared to the vascular walls of animals as set forth above.

Humans implanted with a rapamycin coated stent comprising rapamycin in the same dose range as studied in animal models using the same polymeric matrix, as described above, reveal a much more profound reduction in neointimal hyperplasia than observed in animal models, based on the magnitude and duration of reduction in neointima. The human clinical response to rapamycin reveals essentially total abolition of neointimal hyperplasia inside the stent using both angiographic and intravascular ultrasound measurements. These results are sustained for at least one year as set forth in Table 5 below.

also been determined that rapamycin exerts a local inflammatory effect in the vessel wall when administered from a stent in low doses for a sustained period of time (approximately two to six weeks). The local anti-inflammatory benefit is profound and unexpected. In combination with the smooth

TABLE 5.0

| Patients Treated (N = 45 patients) with a Rapamycin-coated Stent | | |
|---|---|---|
| Effectiveness Measures | Sirolimus FIM (N = 45 Patients, 45 Lesions) | 95% Confidence Limit |
| Procedure Success (QCA) | 100.0% (45/45) | [92.1%, 100.0%] |
| 4-month In-Stent Diameter Stenosis (%) | | |
| Mean ± SD (N) | 4.8% ± 6.1% (30) | [2.6%, 7.0%] |
| Range (min, max) | (−8.2%, 14.9%) | |
| 6-month In-Stent Diameter Stenosis (%) | | |
| Mean ± SD (N) | 8.9% ± 7.6% (13) | [4.8%, 13.0%] |
| Range (min, max) | (−2.9%, 20.4%) | |
| 12-month In-Stent Diameter Stenosis (%) | | |
| Mean ± SD (N) | 8.9% ± 6.1% (15) | [5.8%, 12.0%] |
| Range (min, max) | (−3.0%, 22.0%) | |
| 4-month In-Stent Late Loss (mm) | | |
| Mean ± SD (N) | 0.00 ± 0.29 (30) | [−0.10, 0.10] |
| Range (min, max) | (−0.51, 0.45) | |
| 6-month In-Stent Late Loss (mm) | | |
| Mean ± SD (N) | 0.25 ± 0.27 (13) | [0.10, 0.39] |
| Range (min, max) | (−0.51, 0.91) | |
| 12-month In-Stent Late Loss (mm) | | |
| Mean ± SD (N) | 0.11 ± 0.36 (15) | [−0.08, 0.29] |
| Range (min, max) | (−0.51, 0.82) | |
| 4-month Obstruction Volume (%) (IVUS) | | |
| Mean ± SD (N) | 10.48% ± 2.78% (28) | [9.45%, 11.51%] |
| Range (min, max) | (4.60%, 16.35%) | |
| 6-month Obstruction Volume (%) (IVUS) | | |
| Mean ± SD (N) | 7.22% ± 4.60% (13) | [4.72%, 9.72%], |
| Range (min, max) | (3.82%, 19.88%) | |
| 12-month Obstruction Volume (%) (IVUS) | | |
| Mean ± SD (N) | 2.11% ± 5.28% (15) | [0.00%, 4.78%], |
| Range (min, max) | (0.00%, 19.89%) | |
| 6-month Target Lesion Revascularization (TLR) | 0.0% (0/30) | [0.0%, 9.5%] |
| 12-month Target Lesion Revascularization (TLR) | 0.0% (0/15) | [0.0%, 18.1%] |

QCA = Quantitative Coronary Angiography
SD = Standard Deviation
IVUS = Intravascular Ultrasound Rapamycin produces an unexpected benefit in humans when delivered from a stent by causing a profound reduction in in-stent neointimal hyperplasia that is sustained for at least one year. The magnitude and duration of this benefit in humans is not predicted from animal model data.

These results may be due to a number of factors. For example, the greater effectiveness of rapamycin in humans is due to greater sensitivity of its mechanism(s) of action toward the pathophysiology of human vascular lesions compared to the pathophysiology of animal models of angioplasty. In addition, the combination of the dose applied to the stent and the polymer coating that controls the release of the drug is important in the effectiveness of the drug.

As stated above, rapamycin reduces vascular hyperplasia by antagonizing smooth muscle proliferation in response to mitogenic signals that are released during angioplasty injury. Also, it is known that rapamycin prevents T-cell proliferation and differentiation when administered systemically. It has muscle anti-proliferative effect, this dual mode of action of rapamycin may be responsible for its exceptional efficacy.

Accordingly, rapamycin delivered from a local device platform, reduces neointimal hyperplasia by a combination of anti-inflammatory and smooth muscle anti-proliferative effects. Local device platforms include stent coatings, stent sheaths, grafts and local drug infusion catheters, porous or non-porous balloons or any other suitable means for the in situ or local delivery of drugs, agents or compounds. For example, as set forth subsequently, the local delivery of drugs, agents or compounds may be directly from a coating on a balloon.

The anti-inflammatory effect of rapamycin is evident in data from an experiment, illustrated in Table 6, in which rapamycin delivered from a stent was compared with dexamethasone delivered from a stent. Dexamethasone, a potent steroidal anti-inflammatory agent, was used as a reference standard. Although dexamethasone is able to reduce inflammation scores, rapamycin is far more effective than dexamethasone in reducing inflammation scores. In addition, rapamycin significantly reduces neointimal hyperplasia, unlike dexamethasone.

TABLE 6.0

| Group Rapamycin Rap | N= | Neointimal Area (mm²) | % Area Stenosis | Inflammation Score |
|---|---|---|---|---|
| Uncoated | 8 | 5.24 ± 1.65 | 54 ± 19 | 0.97 ± 1.00 |
| Dexamethasone (Dex) | 8 | 4.31 ± 3.02 | 45 ± 31 | 0.39 ± 0.24 |
| Rapamycin (Rap) | 7 | 2.47 ± 0.94* | 26 ± 10* | 0.13 ± 0.19* |
| Rap + Dex | 6 | 2.42 ± 1.58* | 26 ± 18* | 0.17 ± 0.30* |

*= significance level P < 0.05

Rapamycin has also been found to reduce cytokine levels in vascular tissue when delivered from a stent. The data illustrates that rapamycin is highly effective in reducing monocyte chemotactic protein (MCP-1) levels in the vascular wall. MCP-1 is an example of a proinflammatory/chemotactic cytokine that is elaborated during vessel injury. Reduction in MCP-1 illustrates the beneficial effect of rapamycin in reducing the expression of proinflammatory mediators and contributing to the anti-inflammatory effect of rapamycin delivered locally from a stent. It is recognized that vascular inflammation in response to injury is a major contributor to the development of neointimal hyperplasia.

Since rapamycin may be shown to inhibit local inflammatory events in the vessel it is believed that this could explain the unexpected superiority of rapamycin in inhibiting neointima.

As set forth above, rapamycin functions on a number of levels to produce such desired effects as the prevention of T-cell proliferation, the inhibition of negative remodeling, the reduction of inflammation, and the prevention of smooth muscle cell proliferation. While the exact mechanisms of these functions are not completely known, the mechanisms that have been identified may be expanded upon.

Studies with rapamycin suggest that the prevention of smooth muscle cell proliferation by blockade of the cell cycle is a valid strategy for reducing neointimal hyperplasia. Dramatic and sustained reductions in late lumen loss and neointimal plaque volume have been observed in patients receiving rapamycin delivered locally from a stent. Various embodiments of the present invention expand upon the mechanism of rapamycin to include additional approaches to inhibit the cell cycle and reduce neointimal hyperplasia without producing toxicity.

The cell cycle is a tightly controlled biochemical cascade of events that regulate the process of cell replication. When cells are stimulated by appropriate growth factors, they move from $G_0$ (quiescence) to the G1 phase of the cell cycle. Selective inhibition of the cell cycle in the G1 phase, prior to DNA replication (S phase), may offer therapeutic advantages of cell preservation and viability while retaining anti-proliferative efficacy when compared to therapeutics that act later in the cell cycle i.e. at S, G2 or M phase.

Accordingly, the prevention of intimal hyperplasia in blood vessels and other conduit vessels in the body may be achieved using cell cycle inhibitors that act selectively at the G1 phase of the cell cycle. These inhibitors of the G1 phase of the cell cycle may be small molecules, peptides, proteins, oligonucleotides or DNA sequences. More specifically, these drugs or agents include inhibitors of cyclin dependent kinases (cdk's) involved with the progression of the cell cycle through the G1 phase, in particular cdk2 and cdk4.

Examples of drugs, agents or compounds that act selectively at the G1 phase of the cell cycle include small molecules such as flavopiridol and its structural analogs that have been found to inhibit cell cycle in the late G1 phase by antagonism of cyclin dependent kinases. Therapeutic agents that elevate an endogenous kinase inhibitory protein$^{kip}$ called P27, sometimes referred to as P27$^{kip1}$, that selectively inhibits cyclin dependent kinases may be utilized. This includes small molecules, peptides and proteins that either block the degradation of P27 or enhance the cellular production of P27, including gene vectors that can transfact the gene to produce P27. Staurosporin and related small molecules that block the cell cycle by inhibiting protein kinases may be utilized. Protein kinase inhibitors, including the class of tyrphostins that selectively inhibit protein kinases to antagonize signal transduction in smooth muscle in response to a broad range of growth factors such as PDGF and FGF may also be utilized.

Any of the drugs, agents or compounds discussed herein may be administered either systemically, for example, orally, intravenously, intramuscularly, subcutaneously, nasally or intradermally, or locally, for example, stent coating, stent covering, local delivery catheter or balloon. In addition, the drugs or agents discussed above may be formulated for fast-release or slow release with the objective of maintaining the drugs or agents in contact with target tissues for a period ranging from three days to eight weeks.

As set forth above, the complex of rapamycin and FKPB12 binds to and inhibits a phosphoinositide (PI)-3 kinase called the mammalian Target of Rapamycin or TOR. An antagonist of the catalytic activity of TOR, functioning as either an active site inhibitor or as an allosteric modulator, i.e. an indirect inhibitor that allosterically modulates, would mimic the actions of rapamycin but bypass the requirement for FKBP12. The potential advantages of a direct inhibitor of TOR include better tissue penetration and better physical/chemical stability. In addition, other potential advantages include greater selectivity and specificity of action due to the specificity of an antagonist for one of multiple isoforms of TOR that may exist in different tissues, and a potentially different spectrum of downstream effects leading to greater drug efficacy and/or safety.

The inhibitor may be a small organic molecule (approximate mw<1000), which is either a synthetic or naturally derived product. Wortmanin may be an agent which inhibits the function of this class of proteins. It may also be a peptide or an oligonucleotide sequence. The inhibitor may be administered either sytemically (orally, intravenously, intramuscularly, subcutaneously, nasally, or intradermally) or locally (stent coating, stent covering, local drug delivery catheter). For example, the inhibitor may be released into the vascular wall of a human from a nonerodible polymeric stent coating. In addition, the inhibitor may be formulated for fast-release or slow release with the objective of maintaining the rapamycin or other drug, agent or compound in contact with target tissues for a period ranging from three days to eight weeks.

As stated previously, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Conventional balloon angioplasty is distinguished from drug delivery via balloons in that no drug is imparted by the balloon. Thus, inasmuch as stents prevent at least a portion of the restenosis process, the use of drugs, agents or compounds which prevent inflammation and proliferation, or prevent proliferation by multiple mechanisms, combined with a stent may provide the most efficacious treatment for post-angioplasty restenosis.

Further, insulin supplemented diabetic patients receiving rapamycin eluting vascular devices, such as stents, may exhibit a higher incidence of restenosis than their normal or non-insulin supplemented diabetic counterparts. Accordingly, combinations of drugs may be beneficial.

As used herein, rapamycin includes rapamycin and all analogs, derivatives and conjugates that bind to FKBP12, and other immunophilins and possesses the same pharmacologic properties as rapamycin including inhibition of TOR.

Although the anti-proliferative effects of rapamycin may be achieved through systemic use, superior results may be achieved through the local delivery of the compound. Essentially, rapamycin works in the tissues, which are in proximity to the compound, and has diminished effect as the distance from the delivery device increases. In order to take advantage of this effect, one would want the rapamycin in direct contact with the lumen walls.

As described herein, there are a number of advantages to the local or regional delivery of certain drugs, agents and/or compounds via means other than or in addition to delivery from an implantable medical device. However, the efficacy of the drugs, agents and/or compounds may, to a certain extent, depend on the formulation thereof. The mode of delivery may determine the formulation of the drug. Accordingly, different delivery devices may utilize different formulations. As illustrated above, drugs may be delivered from a stent; however, in other embodiments as described in detail subsequently, any number of devices may be utilized.

It is typically very difficult to create solution dosage forms of water insoluble and lipohilic (having an affinity for and/or tending to combine with lipids) drugs such as rapamycin without resorting to substantial quantities of surfactants, co-solvents and the like. Often times, these excipients (inert substance that acts as a vehicle), such as Tween 20 and 80, Cremophor and polyethylene glycol (PEG) come with varying degrees of toxicity to the surrounding tissue. Accordingly, the use of organic co-solvents such as dimethol sulfoxide (DMSO), N-methylpyrrolidone (NMP) and ethanol need to be minimized to reduce the toxicity of the solvent. Essentially, the key for a liquid formulation of a water insoluble drug is to find a good combination of excipient and co-solvent, and an optimal range of the additives in the final dosage form to balance the improvement of drug solubility and necessary safety margins.

As the outstanding results from clinical trials of recent drug eluting stents such as the Cypher® and Taxus® drug eluting stents demonstrated, a prolonged local high concentration and tissue retention of a potent anti-inflammatory and anti-neoplastic agent released from a stent coating can substantially eliminate the neointimal growth following an angioplasty procedure. Rapamycin, released from the Cypher® stent has consistently demonstrated superior efficacy against restenosis after stent implantation as compared to a bare metal stent. However, there are clinical situations where a non-stent approach for the local delivery or regional delivery may be advantageous, including bifurcated junctions, small arteries and the restenosis of previously implanted stents. Accordingly, there may exist a need for potent therapeutics that only need to be deposited locally or regionally and the drug will exert its pharmacological functions mainly through its good lipophilic nature and long tissue retention property.

A locally or regionally delivered solution of a potent therapeutic agent, such as rapamycin, offers a number of advantages over a systemically delivered agent or an agent delivered via an implantable medical device. For example, a relatively high tissue concentration may be achieved by the direct deposition of the pharmaceutical agent in the arterial wall. Depending on the location of the deposition, a different drug concentration profile may be achieved than through that of a drug eluting stent. In addition, with a locally or regionally delivered solution, there is no need for a permanently implanted device such as a stent, thereby eliminating the potential side affects associated therewith, such as inflammatory reaction and long term tissue damage. It is, however, important to note that the locally or regionally delivered solution may be utilized in combination with drug eluting stents or other coated implantable medical devices. Another advantage of solution or liquid formulations lies in the fact that the adjustment of the excipients in the liquid formulation would readily change the drug distribution and retention profiles. In addition, the liquid formulation may be mixed immediately prior to the injection through a pre-packaged multi-chamber injection device to improve the storage and shelf life of the dosage forms.

In accordance with exemplary embodiments of the present invention, a series of liquid formulations were developed for the local or regional delivery of water insoluble compounds such as sirolimus and its analogs, including CCI-779, ABT-578 and everolimus, through weeping balloons and catheter injection needles. Sirolimus and its analogs are rapamycins. These liquid formulations increase the apparent solubility of the pharmacologically active but water insoluble compounds by two to four orders of magnitude as compared to the solubility limits of the compounds in water. These liquid formulations rely on the use of a very small amount of organic solvents such as Ethanol and a larger amount of safe amphiphilic (of or relating to a molecule having a polar, water soluble group attached to a non-polar, water insoluble hydration chain) excipients such as polyethylene glycol (PEG 200, PEG 400) and vitamin E TPGS to enhance the solubility of the compounds. These liquid formulations of highly water insoluble compounds are stable and readily flowable at room temperature. Certain excipients, such as Vitamin E TPGS and BHT may be utilized to enhance the storage stability of sirolimus compounds through their anti-oxidation properties.

Table 7, shown below, summarizes the concentrations of the excipient, the co-solvents and the drug for four different liquid formulations in accordance with exemplary embodiments of the present invention. The concentrations of each constituent were determined by liquid chromatography and are presented as weight by volume figures. As may be seen from Table 7, a 4 mg/ml concentration of sirolimus was achieved with an ethanol concentration of two percent, a water concentration of twenty-five percent and a PEG 200 concentration of seventy-five percent.

TABLE 7

|  | Formulation B1 | Formulation A1 |
| --- | --- | --- |
| Sirolimus conc. (mg/mL) | 1.79 | 1.0 |
| EtOH conc. (%) | 3.83 | 2 |
| H2O conc. (%) | 7.7 | 25 |
| PEG 200 conc. (%) | 88.5 | 73 |
| Sirolimus conc. (mg/mL) | 2.0 | 4 |
| EtOH conc. (%) | 2.0 | 2.0 |

TABLE 7-continued

|  | Formulation B1 | Formulation A1 |
|---|---|---|
| H2O conc. (%) | 25 | 25 |
| PEG 200 conc. (%) | 75 | 75 |

As set forth above, a liquid formulation comprising 4 mg/ml of sirolimus may be achieved utilizing PEG 200 as the excipient and ethanol and water as the co-solvents. This concentration of sirolimus is about four hundred to about one thousand times higher than the solubility of sirolimus in water. The inclusion of an effective co-solvent, PEG 200, ensures that the high concentration of sirolimus does not start to precipitate out of solution until diluted five to ten fold with water. The high concentration of sirolimus is necessary to maintain an effective and high local concentration of sirolimus after delivery to the site. The liquid formulations are flowable at room temperature and are compatible with a number of delivery devices. Specifically, each of these formulations were successfully injected through an infusion catheter designated by the brand name CRESCENDO™ from Cordis Corporation, Miami, Fla., as described in more detail subsequently, and the EndoBionics Micro Syringe™ Infusion Catheter available from EndoBionics, Inc., San Leandros, Calif., as described in more detail above, in porcine studies.

In another exemplary embodiment, the liquid formulation of sirolimus comprises water and ethanol as co-solvents and Vitamin E TPGS as the excipient. The liquid formulation was created utilizing the following process. Two hundred milligrams of sirolimus and two grams of ethanol were added to a pre-weighed twenty milliliter scintillation vial. The vial was vortexed and sonicated until the sirolimus was completely dissolved. Approximately six hundred milligrams of Vitamin E TPGS was then added to the solution of ethanol and sirolimus. The vial was vortexed again until a clear yellowish solution was obtained. Nitrogen gas was then used to reduce the amount of ethanol in the vial to approximately two hundred twenty-nine milligrams. In a separate vial, three hundred milligrams of Vitamin E TPGS was dissolved in eleven milliliters of purified water while undergoing vortexing. The Vitamin E TPGS and water solution was then added to the first vial containing the sirolimus, Vitamin E TPGS and ethanol. The first vial was then vortexed vigorously and continuously for three minutes. The resulting sirolimus solution was clear with a foam on top. The foam gradually disappeared after sitting at room temperature. An HPLC assay of sirolimus indicated that the sirolimus concentration in the final solution was 15 mg/ml. The final solution had an ethanol concentration of less than two percent, which as stated above is important so as to maintain ethanol as an inactive ingredient. Accordingly, utilizing Vitamin E TPGS as the excipient rather than PEG, resulted in a higher concentration of sirolimus in the final formulation.

Table 8, as shown below, summarizes the composition and visual observations for multiple aqueous formulations of sirolimus utilizing ethanol, Vitamin E TPGS and water at different ratios. The solutions represented by the data contained in Table 8 were generated using essentially the same procedure as described above, except that the ratios between sirolimus and Vitamin E TPGS were varied.

TABLE 8

| Group # | Sirolimus mg | Vitamin E TPGS, mg | Ethanol mg | 13.3 ml water containing Vitamin E TPGS, mg | Observation of final solution |
|---|---|---|---|---|---|
| 1 | 202.7 | 642 | 230 | 320 | Clear |
| 2 | 205.2 | 631 | 260 | 330 | Clear |
| 3 | 201.1 | 618 | 260 | 600 | Clear |
| 4 | 204.1 | 625 | 260 | 590 | Clear |
| 5 | 203.3 | 618 | 250 | 1400 | Hazy to clear, Viscous |
| 6 | 204.5 | 630 | 250 | 1420 | Clear, viscous |

All of the above preparations except for number five remained as stable solutions at both room temperature and under refrigerated condition. The results in Table 8 indicate that, Vitamin E TPGS may be utilized over a wide range of concentrations to increase the solubility of sirolimus in an aqueous solution.

In another exemplary embodiment, a liquid formulation of CCI-779, a sirolimus analog, is prepared utilizing ethanol, Vitamin E TPGS and water. This liquid formulation was made under similar conditions as to that described above. Because of its better solubility in ethanol, only 0.8 grams of ethanol was used to dissolve two hundred milligrams of CCI-779 as opposed to the two grams of sirolimus. After the amount of ethanol was reduced to approximately two hundred thirty milligrams, eleven milliliters of purified water containing three hundred milligrams of Vitamin E TPGS was added to the vial of ethanol and CCI-779. The combined solution was vortexed for three minutes and resulted in a clear solution. An HPLC assay of CCI-779 indicated that the concentration of CCI-779 in the final solution was 15 mg/ml. The concentration of ethanol in the final solution was less than two percent. Accordingly, the results are substantially identical to that achieved for the sirolimus.

As stated above, a number of catheter-based delivery systems may be utilized to deliver the above-described liquid formulations. One such catheter-based system is the CRESCENDO™ infusion catheter. The CRESCENDO™ infusion catheter is indicated for the delivery of solutions, such as heparinized saline and thrombolytic agents selectively to the coronary vasculature. The infusion catheter may also be utilized for the delivery of the liquid formulations, including the liquid solution of sirolimus, described herein. The infusion region includes an area comprised of two inflatable balloons with multiple holes at the catheter's distal tip. The infusion region is continuous with a lumen that extends through the catheter and terminates at a Luer port in the proximal hub. Infusion of solutions is accomplished by hand injection through an infusion port. The catheter also comprises a guidewire lumen and a radiopaque marker band positioned at the center of the infusion region to mark its relative position under fluoroscopy.

A larger amount of safe amphiphilic excipients, such as Vitamin E TPGS, PEG 200, and PEG 400, may be used alone or in combination to enhance the solubility and stability of the drug during the preparation of the formulations. Vitamin E TPGS may also enhance the drug transfer into the local tissues during the deployment of the medical device and contact with a vascular tissue. Enhanced transfer of the drug from the external surfaces and subsequent deposition of the drug in the local tissue provide for a long-term drug effects and positive efficacy such as reduced neointimal formation after an angioplasty procedure or a stent implantation. In addition to improving the solubility of a water-insoluble drug during the formulation preparation, these excipients may also help form a non-crystalline drug formulation on a device surface when the water is substantially dried off, and facilitate a fast detachment of the drug formulation from the coating of a medical device when contacted with a local tissue.

In addition to infusion catheters, these liquid formulations of highly water insoluble compounds are stable and may be used for coating an external surface of a medical device such as a PTCA balloon.

Alternately, stable solutions, suspensions or emulsions of water insoluble compounds may be formed utilizing similar solubility-enhancing agents to obtain a higher drug concentration than the formulations set forth above for coating the external surfaces of a medical device. The pH value of these suspensions or emulsions may be adjusted to improve the stability of the drug formulations.

The viscosity of the liquid formulations can be adjusted by changing the mixture ratio of PEG and Vitamin E TPGS. Also, additional excipients may be included without substantially affecting the viscosity of the final coating solution but improve the stability of the drug in the formulation and coating.

Although anti-restenotic agents have been primarily described herein, the present invention may also be used to deliver other agents alone or in combination with anti-restenotic agents. Some of the therapeutic agents for use with the present invention which may be transmitted primarily luminally, primarily murally, or both and may be delivered alone or in combination include, but are not limited to, antiproliferatives, antithrombins, immunosuppressants including sirolimus, antilipid agents, anti-inflammatory agents, antineoplastics, antiplatelets, angiogenic agents, anti-angiogenic agents, vitamins, antimitotics, metalloproteinase inhibitors, NO donors, estradiols, anti-sclerosing agents, and vasoactive agents, endothelial growth factors, estrogen, beta blockers, AZ blockers, hormones, statins, insulin growth factors, antioxidants, membrane stabilizing agents, calcium antagonists, retenoid, bivalirudin, phenoxodiol, etoposide, ticlopidine, dipyridamole, and trapidil alone or in combinations with any therapeutic agent mentioned herein. Therapeutic agents also include peptides, lipoproteins, polypeptides, polynucleotides encoding polypeptides, lipids, protein-drugs, protein conjugate drugs, enzymes, oligonucleotides and their derivatives, ribozymes, other genetic material, cells, antisense, oligonucleotides, monoclonal antibodies, platelets, prions, viruses, bacteria, and eukaryotic cells such as endothelial cells, stem cells, ACE inhibitors, monocyte/macrophages or vascular smooth muscle cells to name but a few examples. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the therapeutic layer. Therapeutic agents may also be radioactive isotopes or agents activated by some other form of energy such as light or ultrasonic energy, or by other circulating molecules that can be systemically administered.

Therapeutic agents may perform multiple functions including modulating angiogenesis, restenosis, cell proliferation, thrombosis, platelet aggregation, clotting, and vasodilation.

Anti-inflammatories include but are not limited to nonsteroidal anti-inflammatories (NSAID), such as aryl acetic acid derivatives, e.g., Diclofenac; aryl propionic acid derivatives, e.g., Naproxen; and salicylic acid derivatives, e.g., Diflunisal. Anti-inflammatories also include glucocoriticoids (steroids) such as dexamethasone, aspirin, prednisolone, and triamcinolone, pirfenidone, meclofenamic acid, tranilast, and nonsteroidal anti-inflammatories. Anti-inflammatories may be used in combination with antiproliferatives to mitigate the reaction of the tissue to the antiproliferative.

The agents may also include anti-lymphocytes; anti-macrophage substances; immunomodulatory agents; cyclooxygenase inhibitors; anti-oxidants; cholesterol-lowering drugs; statins and angiotens in converting enzyme (ACE); fibrinolytics; inhibitors of the intrinsic coagulation cascade; antihyperlipoproteinemics; and anti-platelet agents; anti-metabolites, such as 2-chlorodeoxy adenosine (2-CdA or cladribine); immuno-suppressants including sirolimus, everolimus, tacrolimus, etoposide, and mitoxantrone; anti-leukocytes such as 2-CdA, IL-1 inhibitors, anti-CD116/CD18 monoclonal antibodies, monoclonal antibodies to VCAM or ICAM, zinc protoporphyrin; anti-macrophage substances such as drugs that elevate NO; cell sensitizers to insulin including glitazones; high density lipoproteins (HDL) and derivatives; and synthetic facsimile of HDL, such as lipator, lovestatin, pranastatin, atorvastatin, simvastatin, and statin derivatives; vasodilators, such as adenosine, and dipyridamole; nitric oxide donors; prostaglandins and their derivatives; anti-TNF compounds; hypertension drugs including Beta blockers, ACE inhibitors, and calcium channel blockers; vasoactive substances including vasoactive intestinal polypeptides (VIP); insulin; cell sensitizers to insulin including glitazones, P par agonists, and metformin; protein kinases; antisense oligonucleotides including resten-NG; antiplatelet agents including tirofiban, eptifibatide, and abciximab; cardio protectants including, VIP, pituitary adenylate cyclase-activating peptide (PACAP), apoA-I milano, amlodipine, nicorandil, cilostaxone, and thienopyridine; cyclooxygenase inhibitors including COX-1 and COX-2 inhibitors; and petidose inhibitors which increase glycolitic metabolism including omnipatrilat. Other drugs which may be used to treat inflammation include lipid lowering agents, estrogen and progestin, endothelin receptor agonists and interleukin-6 antagonists, and Adiponectin.

Agents may also be delivered using a gene therapy-based approach in combination with an expandable medical device. Gene therapy refers to the delivery of exogenous genes to a cell or tissue, thereby causing target cells to express the exogenous gene product. Genes are typically delivered by either mechanical or vector-mediated methods.

Some of the agents described herein may be combined with additives which preserve their activity. For example additives including surfactants, antacids, antioxidants, and detergents may be used to minimize denaturation and aggregation of a protein drug. Anionic, cationic, or nonionic surfactants may be used. Examples of nonionic excipients include but are not limited to sugars including sorbitol, sucrose, trehalose; dextrans including dextran, carboxy methyl (CM) dextran, diethylamino ethyl (DEAE) dextran; sugar derivatives including D-glucosaminic acid, and D-glucose diethyl mercaptal; synthetic polyethers including polyethylene glycol (PEO) and polyvinyl pyrrolidone (PVP); carboxylic acids including D-lactic acid, glycolic acid, and propionic acid; surfactants with affinity for hydrophobic interfaces including n-dodecyl-.beta.-D-maltoside, n-octyl-.beta.-D-glucoside, PEO-fatty acid esters (e.g. stearate (myrj 59) or oleate), PEO-sorbitan-fatty acid esters (e.g. Tween 80, PEO-20 sorbitan monooleate), sorbitan-fatty acid esters (e.g. SPAN 60, sorbitan monostearate), PEO-glyceryl-fatty acid esters; glyceryl fatty acid esters (e.g. glyceryl monostearate), PEO-hydrocarbon-ethers (e.g. PEO-10 oleyl ether; triton X-100; and Lubrol. Examples of ionic detergents include but are not limited to fatty acid salts including calcium stearate, magnesium stearate, and zinc stearate; phospholipids including lecithin and phosphatidyl choline; (PC) CM-PEG; cholic acid; sodium dodecyl sulfate (SDS); docusate (AOT); and taumocholic acid.

Although antioxidants may be utilized with any number of drugs, including all the drugs described herein, exemplary embodiments of the invention are described with respect to rapamycin and more specifically, drug eluting implantable medical devices comprising rapamycin. As briefly set forth above, molecules or specific portions of molecules may be particularly sensitive to oxidation. In rapamycins, the conjugated triene moiety of the molecule is particularly susceptible to oxidation. Essentially, oxygen breaks the carbon chain of the conjugate triene moiety and the bioactivity of the rapamycin is degraded. In addition, as is typical with oxidation processes, the drug is broken down into one or more different compounds. Accordingly, it may be particularly advantageous to mix or co-mingle an antioxidant with the rapamycin. Specifically, in order to achieve the best results, it is important to co-mingle the antioxidant and the drug to the greatest extent possible. More importantly, the physical positioning of the antioxidant proximate to the drug is the key to success. The antioxidant preferably remains free to combine with oxygen so that the oxygen does not break up the moiety and ultimately degrade the drug. Given that the rapamycin may be incorporated into a polymeric coating or matrix, it is particularly important that the antioxidant be maintained proximate to the drug rather than the polymer(s). Factors that influence this include the constituents of the polymeric matrix, the drug, and how the polymer/drug coating is applied to the implantable medical device. Accordingly in order to achieve the desired result, selection of the appropriate antioxidant, the process of mixing all of the elements and the application of the mixture is preferably tailored to the particular application.

In accordance with exemplary embodiments of the invention, a number of antioxidants were tested to determine their efficacy in preventing the degradation of rapamycin, or more specifically, sirolimus. Screening experiments were performed to evaluate the solubility of various antioxidants in tetrahydroxyfuran (THF) solutions containing sirolimus and the percentage of antioxidant required to prevent oxidation of sirolimus alone and in a basecoat polymeric matrix. THF is the solvent in which sirolimus may be dissolved. It is important to note that other solvents may be utilized. Two sets of controls were utilized. Control #1 comprises solutions of THF and sirolimus and/or polymers with no antioxidant, and Control #2 comprises solutions of THF and sirolimus and/or polymers, wherein the THF contains a label claim of 250 ppm of BHT as a stabilizer from the vendor of THF. In other words, the BHT is an added constituent of the THF solvent to prevent oxidation of the solvent. Table 9 shown below is a matrix of the various mixtures. All percentages are given as weight/volume.

TABLE 9

| Antioxidant | Target % Antioxidant | Antioxidant Grams/ 50 mL | Target % Antioxidant | Antioxidant Grams/ 50 mL |
|---|---|---|---|---|
| Ascorbic Acid | 0.02 | 0.01 | 0.5 | 0.25 |
| Ascorbyl Palmitate | 0.01 | 0.005 | 0.02 | 0.01 |
| BHT | 0.005 | 0.0025 | 0.02 | 0.01 |
| Tocopherol | 0.05 | 0.025 | 0.075 | 0.0375 |
| Control #1 | 0.0 | 0.0 | 0.0 | 0.0 |
| Control #2 | 250 ppm BHT | 0.0 | 0.0 | 0.0 |

Table 10, shown below, identifies the samples for evaluation. All percentages are given as weight/volume. The samples in Table 10 contain no polymer. Table 11, also shown below, identifies the samples for evaluation with the solutions now comprising polymers, including PBMA and PEVA.

TABLE 10

Solutions with Sirolimus Only-No Polymers

| SAMPLE ID # | ACTUAL % ANTIOXIDANT |
|---|---|
| AA1A | 0.026 Ascorbic Acid |
| AA2A | 0.50 Ascorbic Acid |
| AP1A | 0.01 Ascorbyl Palmitate |
| AP2A | 0.02 Ascorbyl Palmitate |
| BHT1A | 0.006 BHT |
| BHT2A | 0.02 BHT |
| C2A | Control #2 - 250 ppm BHT |
| TP1A | 0.048 Tocopherol |
| TP2A | 0.082 Tocopherol |
| C1A | Control #1 |

TABLE 11

Solutions with Sirolimus and Polymers

| SAMPLE ID # | ACTUAL % ANTIOXIDANT |
|---|---|
| AA1B | 0.022 Ascorbic Acid |
| AA2B | 0.508 Ascorbic Acid |
| AP1B | 0.01 Ascorbyl Palmitate |
| AP2B | 0.02 Ascorbyl Palmitate |
| BHT1B | 0.006 BHT |
| BHT2B | 0.02 BHT |
| C2B | Control #2 - 250 ppm BHT |
| TP1B | 0.054 Tocopherol |
| TP2B | 0.102 Tocopherol |
| C1B | Control #1 |

As set forth above, each of the samples in Tables 10 and 11 were tested to determine the solubility of the various antioxidants as well as their effectiveness in preventing drug degradation. All of the antioxidants were soluble in both the solvent with sirolimus solutions and the solvent with sirolimus and polymer solutions. The solubility of each of the antioxidants was determined by a visual inspection of the test samples.

Table 12, as shown below, identifies the chosen samples that were evaluated for drug content (percent label claim or % LC) after five (5) days in an oven set at a temperature of sixty degrees C. (60° C.). The samples were evaluated after five (5) days utilizing a drug testing assay for sirolimus. In the exemplary embodiment, a HPLC assay was utilized. The important numbers are the percent label claim number (% LC) of the solutions that indicates how much of the drug remains or is recovered. The antioxidants, BHT, Tocopherol, and/or Ascorbic Acid provided significant protection against the harsh environmental conditions of the test. Lower % LC numbers are evident in solutions samples that do not contain an antioxidant.

TABLE 12

Solutions with Sirolimus and Polymers after 5 days 60° C. storage

| SAMPLE ID # | ACTUAL % ANTIOXIDANT | % LC |
|---|---|---|
| AA2B | 0.508 Ascorbic Acid | 96.4 |
| AP2B | 0.02 Ascorbyl Palmitate | 82.5 |
| BHT2B | 0.02 BHT | 94.8 |
| TP2B | 0.102 Tocopherol | 97.3 |
| C2B | Control #2 - 250 ppm BHT | 99.5 |
| C1B | Control #1 | 70.0 |
| C1B | Control #1 | 69.2 |

As shown below, Table 13 provides the % LC results for the samples without polymers and Table 14 provides the % LC results for the samples with polymer after four (4) weeks of sixty degrees C. (60° C.).

TABLE 13

| SAMPLE ID # | CALCULATED RESULTS (µg/ml) | THEORETICAL CONCENTRATION (µg/ml) | % LC |
|---|---|---|---|
| AA1A | 1155.56 | 1669.2 | 69.2 |
| AA2A | 1280.90 | 1669.2 | 76.7 |
| AP1A | 851.45 | 1669.2 | 51.0 |
| AP2A | 939.36 | 1669.2 | 56.3 |
| BHT1A | 437.38 | 1669.2 | 26.2 |
| BHT2A | 1434.98 | 1669.2 | 86.0 |
| TP1A | 1335.58 | 1669.2 | 80.0 |
| TP2A | 1618.61 | 1669.2 | 97.0 |
| C1A #1 | 608.64 | 1669.2 | 36.5 |
| C1A #2 | 552.57 | 1669.2 | 33.1 |
| C2A #1 | 1794.70 | 1669.2 | 107.5 |
| C2A #2 | 1794.67 | 1669.2 | 107.5 |

TABLE 14

| SAMPLE ID # | CALCULATED RESULTS (µg/ml) | THEORETICAL. CONCENTRATION (µg/ml) | % LC |
|---|---|---|---|
| AA1B | 884.95 | 1669.2 | 53.0 |
| AA2B | 1489.70 | 1669.2 | 89.2 |
| AP1B | 743.98 | 1669.2 | 44.6 |
| AP2B | 906.76 | 1669.2 | 54.3 |
| BHT1B | 595.18 | 1669.2 | 35.7 |
| BHT2B | 1396.55 | 1669.2 | 83.7 |
| TP1B | 1177.30 | 1669.2 | 70.5 |
| TP2B | 1695.45 | 1669.2 | 101.6 |
| C1B #1 | 490.56 | 1669.2 | 29.4 |
| C1B #2 | 470.15 | 1669.2 | 28.2 |
| C2B #1 | 1807.44 | 1669.2 | 108.3 |
| C2B #2 | 1810.41 | 1669.2 | 108.5 |

As seen from a review of the % LC or drug recovery enumerated in Tables 13 and 14, higher percent concentrations of Tocopherol, BHT, and/or Ascorbic Acid provide significant protection against the harsh environmental conditions of the test. However, higher % LC numbers are evident in all controls containing 250 ppm BHT due to possible solution evaporation of the samples from loose caps on the samples in the 60° C. storage condition.

Additional samples were tested under ambient conditions, rather than at 60° C., and using the same compositions; however, the test period was expanded to seven weeks. The results are given in Table 15, shown below.

TABLE 15

| SAMPLE ID # | CALCULATED RESULTS (µg/ml) | THEORETICAL CONCENTRATION (µg/ml) | % LC |
|---|---|---|---|
| C1A | 1248.04 | 1669.2 | 74.8 |
| C2A | 1578.15 | 1669.2 | 94.5 |
| C1BMS | 1376.46 | 1669.2 | 82.5 |
| C1BMS | 1377.20 | 1669.2 | 82.5 |
| C2B | 1633.07 | 1669.2 | 97.8 |
| TP1A | 1635.54 | 1669.2 | 98.0 |
| TP2A | 1632.05 | 1669.2 | 97.8 |
| TP1B | 1631.75 | 1669.2 | 97.8 |
| TP2B | 1621.64 | 1669.2 | 97.2 |
| AA1A | 1590.17 | 1669.2 | 95.3 |
| AA2A | 1578.21 | 1669.2 | 94.5 |
| AA1B | 1598.79 | 1669.2 | 95.8 |
| AA2B | 1592.47 | 1669.2 | 95.4 |
| AP1A | 1429.76 | 1669.2 | 87.7 |
| AP2A | 1415.83 | 1669.2 | 84.8 |
| AP1B | 1472.45 | 1669.2 | 88.2 |
| AP2B | 1480.31 | 1669.2 | 88.7 |
| BHT1A | 1527.18 | 1669.2 | 91.5 |
| BHT2A | 1601.72 | 1669.2 | 96.0 |
| BHT1B | 1579.50 | 1669.2 | 94.6 |
| BHT2B | 1614.52 | 1669.2 | 96.7 |

As may be seen from a review of Table 15, the results are substantially similar to those obtained for five (5) days and four (4) weeks at sixty degrees C. (60° C.) % LC data. Accordingly, in a preferred exemplary embodiment, Tocopherol, BHT and/or Ascorbic Acid may be utilized to substantially reduce drug degradation due to oxidation.

Referring to FIG. 1, there is illustrated in graphical format, the results of the same drug screening as described above with the solution applied to a cobalt-chromium, 18 mm stent. In this test, two sets of solution samples were utilized, one with sirolimus and polymer solution containing the antioxidant and one with sirolimus and polymer solution containing no antioxidant. The antioxidant utilized was 0.02 weight percent BHT per total basecoat solids. The test was utilized to determine the percent drug content change over a time period of 0 to 12 weeks under two conditions; namely, 40° C. with 75 percent relative humidity, and ambient conditions (25° C.). As can be seen from the chart, the addition of BHT to the solution lessens drug degradation at both 8 weeks and 12 weeks under ambient conditions. Accordingly, if one does not stabilize the base coat solution, other process techniques must be utilized; namely, refrigeration and/or vacuum drying.

In accordance with another exemplary embodiment, balloons or other inflatable or expandable devices may be temporarily positioned within a body to deliver a therapeutic agent and/or combination of therapeutic agents and then removed. The therapeutic agents may include liquid formulations of rapamycins as described above or any other formulations thereof. This type of delivery device may be particularly advantageous in the vasculature where stents may not be suitable, for example, in the larger vessels of the peripheral vascular system and at bifurcation points in the vasculature, or where the long term scaffolding of a stent is not required or desired.

In use, the balloon or other inflatable or expandable device may be coated with one or more liquid formulations of therapeutic agents(s) and delivered to a treatment site. The act of inflation or expansion would force the therapeutic agents into the surrounding tissue. The device may be kept in position for a period of between ten seconds to about five minutes depending upon the location. If utilized in the heart, shorter durations are required relative to other areas such as the leg.

The balloon or other inflatable device may be coated in any suitable manner including dipping and spraying as described above. In addition, various drying steps may also be utilized. If multiple coats are required for a specific dosage, then additional drying steps may be utilized between coats.

In accordance with another embodiment, a solution formulation of a rapamycin may be created for use as a coating on the surface of a balloon, as opposed to a stent or through a weeping balloon or infusion catheter. These formulations have a higher concentration of rapamycin than those described above.

As set forth herein, aqueous solutions of sirolimus, with solubility enhancers such as polymers of various molecular weight, PEG 400, PEG 1000, PEG 1500, PEG 2000, vitamin E and its derivatives vitamin E TPGS, non-ionic surfactants including Triton X, alky poly(ethylene oxide), Tween 20, Tween 80, and Brij 35. Low molecular weight anionic surfactant such as sodium dodecyl sulfate, cationic surfactants such as benzalkonium chloride, non-ionic surfactants such as lauryl myristate, lauryl palmitate, etc. may be used to create coating solutions or emulsions for balloon coating.

Experimentation is required to obtain the optimal formulations for the particular coating purpose such that the coating solutions would dry up within a required time and the coating morphology would be stable on a balloon surface. But in general, these aqueous formulations are especially advantageous as a surface balloon coating in that the water content in the coating formulations (from 10% water to 90% water in the solutions) serves to decrease the ability of an organic solvent such as acetone or DMSO to swell and even dissolve the balloons which are made from Nylon, Polyester, PBAX and the like. These aqueous solutions will also cause less damage to the physical and chemical properties of balloons during and after the coating processes as compared to pure organic solvent based formulations.

In addition to the solubility enhancers described herein, water miscible organic solvents such as ethanol, methanol, acetone, acetonitrile (ACN), methyl ethyl ketone (MEK), dimethylsulfoxide (DMSO) and dimethylformamide (DMF) may be used initially to dissolve the drug and establish a homogeneous solution before water is added to make a coating solution with specific concentrations for use as a surface balloon coating. A proper titration of the ratio between the organic solvent and water will also help adjust the concentration of drug in the coating solution, amount of coating put on the balloons, drying time for each coating steps, and eventually the coating morphology and physical integrity of the coating with the drug.

In addition to the solubility enhancers and the organic solvents described herein, other polymeric or non-volatile dissolution enhancing agents may be further added to enhance the formulations. The most useful ones as discussed herein are vitamin E TPGS, polyvinyl alcohol (PVA), microcrystalline cellulose, phospholipids, triglycerides, dextran, heparin and the like. Other antioxidant excipients can also be used in the formulations to stabilize the sirolimus (rapamycin) in the coating. Such antioxidants include BHT, BHA, vitamin E, vitamin E TPGS, ascorbic acid (vitamin C), ascorbyl palmitate, ascorbyl myristate, resveratrol and its many synthetic and semi-synthetic derivatives and analogs, etc. These antioxidant excipients may also serve additional functions such as facilitating the release of drug coatings from the balloon surface upon contact with the artery wall. These and other similar excipients will remain in the coating after the drying processes and serve to speed up the drug in the coating from detaching from the balloon surface at the disease site.

The enhancement of drug coating separation from the balloon through the use of these agents is possibly caused by their inherent tendency to absorb water upon placement in the physiological situation such as inside the arteries. The swelling and physical expansion of the coating at the delivery site will help increase the delivery efficiency of the drug coating into the diseased arterial tissue. Depending on the nature of the particular excipients they may also have the added benefits of enhancing the drug transport from the coating into the diseased cells and the tissues. For instance, vasodilators such as cilostazol and dipyridamole, may also be used as excipients to improve the intracellular transport of the drugs. Also certain excipients may also enhance the cross-membrane transport and even sequestration of the drugs into the local tissues.

The balloon coating conditions may also play important roles in creating the optimal morphology of the final drug coating in that the drying speed of the drug coating matrix on the balloons, the exposure time of subsequent coating time (second, third, fourth coatings, etc. if needed) may re-dissolve the previously laid coating layers. A variation of the current invention is that coating formulations with gradually increasing water content may be used in subsequent coating steps to minimize the coatings laid down previously and increase coating weight and uniformity of each coating step. The final coating solution may even be an emulsion (high water content, and/or high drug content) as opposed to clear aqueous solutions (high organic solvent content) to complete the coating processes.

The following experiments serve to illustrate the principles and formulations described above. Many of the excipients may be interchanged to enhance one aspect or another of the formulations, without affecting the efficacy of the particular formulation.

In a first experiment, an aqueous coating solution using PEG 400 and BHT as the solubility and transport enhancers was formulated. To a tared 10-ml scintillation vial was added about 100.5 mg of sirolimus (rapamycin, stock # 124623500 batch # RB5070)), followed by about 9.8 mg of PEG 400 (Aldrich), and 10.1 mg of BHT (Aldrich). One ml of ethanol was then added to dissolve the above components under shaking. Once the solution became completely clear, 1-ml of water was slowly added to the solution. The mixed solution became cloudy and sirolimus in the organic solution was immediately precipitated out. Sirolimus remained insoluble upon agitation. The composition of the coating formulation is shown in Table 16.

TABLE 16

Aqueous coating solution using PEG 400, BHT (A1 formulation)

|  | Formulation A1 | Actual amt in 2 mL solution |
|---|---|---|
| Sirolimus conc (mg/ml) | 50 | 100.5 mg |
| PEG 400 (mg/ml) | 5 | 9.8 mg |
| BHT (mg/ml) | 5 | 10.1 mg |
| EtOH (%) | 50 | 1 ml |
| H2O (%) | 50 | 1 ml |

No further experimentation on this particular formula was done because of the insolubility of the sirolimus.

In a second experiment, an aqueous coating solution using PEG 400 and BHT as the solubility and transport enhancers was formulated. To a tared 10-ml scintillation vial was added about 99.0 mg of sirolimus (rapamycin, stock # 124623500 batch # RB5070)), followed by about 10.1 mg of PEG 400 (Aldrich), and 9.9 mg of BHT (Aldrich). One and half ml (1.5 ml) of ethanol was then added to dissolve the above components under shaking. Once the solution became completely clear, 0.5-ml of water was slowly added to the solution. The mixed solution remained clear and stable upon agitation. The composition of the coating formulation is shown in Table 17.

TABLE 17

Aqueous coating solution using PEG 400, BHT (A3)

|  | Formulation A3 | Actual amt in 2 mL solution |
|---|---|---|
| Sirolimus conc (mg/ml) | 50 | 99 mg |
| PEG 400 (mg/ml) | 5 | 10.1 mg |
| BHT (mg/ml) | 5 | 9.9 mg |
| EtOH (%) | 75 | 1.5 ml |
| H2O (%) | 25 | 0.5 ml |

The clear solution formulation of Table 17 was transferred to a glass slide for coating morphology studies. A Gilson pipetteman was used to transfer 20 ul of the coating solution onto a pre-weighed glass slide three times. The coating spots on the slides were allowed to dry at room temperature in a laminar hood. The coating spots gradually become opaque after drying. The weight of the slides with coated spots were measured and recorded in lines 1 and 4 of Table 18. The drug content transfer efficiency of the coating solution was determined to be approximately 95 percent.

agitation, part of the drug precipitated out of the solution and stuck to the vial wall. The composition of the coating formulation is shown in Table 19.

TABLE 19

Aqueous coating formulation using PEG 1000, BHT (A5)

|  | Formulation A5 | Actual am in 2 mL solution |
|---|---|---|
| Sirolimus conc (mg/ml) | 50 | 101.0 |
| PEG 1000 (mg/ml) | 5 | 10.0 |
| BHT (mg/ml) | 5 | 10.2 |
| EtOH (%) | 65 | 1.3 |
| H2O | 35 | 0.7 |

The clear portion of the solution of the formulation of Table 19 was transferred to a glass slide for coating morphology studies. A Gilson pipetteman was used to transfer 20 ul of the coating solution onto a pre-weighed glass slide three times. The coating spots on the slides were allowed to dry at room temperature in a laminar hood. The coating spots gradually become opaque after drying. The weight of the slides with coated spots were measured and recorded in lines 5 and 7 of Table 18. The drug content transfer efficiency of the coating solution was determined to be approximately 76 percent. The decreased efficiency of drug transfer was mostly like caused by the precipitation of sirolimus from the solution upon the addition of water. This formulation is not suitable for coating since the weight of final coating is not easily controlled.

TABLE 18

Coating formulations and weight of coated glass slides

| Glass slide # | Tare weight (g) | wt after coating | coating weight (g) | coat wt in mg | coating solution vol (ul) | theor amt (mg) | Transfer eff (%) | Note |
|---|---|---|---|---|---|---|---|---|
| 1 (A3) | 4.7626 | 4.7653 | 0.0027 | 2.70 | 3 × 20 ul | 2.85 | 94.7 | clear solution |
| 2 (B1) | 4.7614 | 4.7640 | 0.0026 | 2.60 | 3 × 20 ul | 2.85 | 91.2 | stable emulsion |
| 3 (B1) | 4.7444 | 4.7491 | 0.0047 | 4.70 | 100 ul | 4.75 | 98.9 | stable emulsion |
| 4 (A3) | 4.7665 | 4.7714 | 0.0049 | 4.90 | 100 ul | 4.95 | 99.0 | clear solution |
| 5 (A5) | 4.7666 | 4.7689 | 0.0023 | 2.30 | 3 × 20 ul | 3.03 | 75.9 | partial precipitation |
| 6 (C1) | 4.7347 | 4.7371 | 0.0024 | 2.40 | 50 ul | 2.51 | 95.6 | clear solution |
| 7 (A5) | 4.7367 | 4.7397 | 0.003 | 3.00 | 100 ul | 5.05 | 59.4 | partial precipitation |
| 8 | 4.8726 | discarded |  |  |  |  |  |  |
| 9 (B1) | 4.7716 | 4.7739 | 0.0023 | 2.30 | 50 ul | 2.38 | 96.6 | stable emulsion |
| 10 (C1) | 4.7646 | 4.7742 | 0.0096 | 4.80 | 100 ul | 5.05 | 95.0 | clear solution |

In a third experiment, an aqueous coating solution using PEG 400 and BHT as the solubility and transport enhancers was formulated. To a tared 10-ml scintillation vial was added about 101.0 mg of sirolimus (rapamycin, stock # 124623500 batch # RB5070)), followed by about 10.0 mg of PEG 1000 (Aldrich), and 10.2 mg of BHT (Aldrich). One point three ml (1.3 ml) of acetone was then added to dissolve the above components under shaking. Once the solution became completely clear, 0.7-ml of water was slowly added to the solution. The mixed solution immediately became cloudy. Upon In a fourth experiment, an aqueous coating solution using PEG 400 and BHT as the solubility and transport enhancers was formulated. To a tared 10-ml scintillation vial was added about 95.5 mg of sirolimus (rapamycin, stock # 124623500 batch # RB5070)), followed by about 9.9 mg of PEG 400 (Aldrich), and 10.2 mg of BHT (Aldrich). One point two ml (1.2 ml) of acetone was then added to dissolve the above components under shaking. Once the solution became completely clear, 0.8-ml of water was slowly added to the solution. The mixed solution immediately became cloudy and remained as a stable emulsion at room temperature. The composition of the coating formulation is shown in Table 20.

TABLE 20

Aqueous coating formulation using PEG 400, BHT (B1)

|  | Formulation B1 | actual am in 2 mL solution |
|---|---|---|
| Sirolimus conc (mg/ml) | 50 | 95.5 |
| PEG 400 (mg/ml) | 5 | 9.9 |
| BHT (mg/ml) | 5 | 10.2 |
| Acetone (%) | 60 | 1.2 |
| H2O (%) | 40 | 0.8 |

The stable emulsion of the formulation of Table 20 was transferred to a glass slide for coating morphology studies. A Gilson pipetteman was used to transfer 20 ul of the coating solution onto a pre-weighed glass slide three times. The coating spots on the slides were allowed to dry at room temperature in a laminar hood. The coating spots gradually become opaque after drying. The weight of the slides with coated spots were measured and recorded in line 2 of Table 18. Coating solution B1 was similarly transferred to glass slides with various amounts, with the results recorded in lines 3 and 9 of Table 18, to test the effects of drying speed on the coating appearance and morphology. The drug content transfer efficiency of the coating solution was determined to be over 90 percent. The small transferred amounts in line 2 gave the better coating morphology in that the coating membrane is clear, most transparent and even on the slides. When larger amounts of the coating emulsion were transferred to the slides, lines 3 and 9, the coating became slightly opaque. The results suggested that it may be beneficial in the coating of slides and balloons that multiple passes be utilized to achieve the best coating morphology and appearances.

In a fifth experiment, an aqueous coating solution using PEG 400 and BHT as the solubility and transport enhancers was formulated. To a tared 10-ml scintillation vial was added about 100.5 mg of sirolimus (rapamycin, stock # 124623500 batch # RB5070), followed by about 10.1 mg of PEG 400 (Aldrich), and 9.9 mg of BHT (Aldrich). One point five ml (1.5 ml) of acetone was then added to dissolve the above components under shaking. Once the solution became completely clear, 0.5-ml of water was slowly added to the solution. The mixed solution remained a clear and stable solution at room temperature. The composition of the coating formulation is shown in Table 21.

TABLE 21

Aqueous coating formulation using PEG 400, BHT (C1)

|  | Formulation C1 | Actual am in 2 mL solution |
|---|---|---|
| Sirolimus conc (mg/ml) | 50 | 100.5 |
| PEG 1000 | 25 | 10.1 |
| BHT (mg/ml) | 5 | 9.9 |
| Acetone (%) | 75 | 1.5 |
| H2O (%) | 25 | 0.5 |

The clear solution of the formulation of Table 21 was transferred to a glass slide for coating morphology studies. A Gilson pipetteman was used to transfer 50 ul of the coating solution onto a pre-weighed glass slide. The coating spot on the slides was allowed to dry at room temperature in a laminar hood. The coating spots gradually become opaque after drying. The weight of the slides with coated spots were measured and recorded in line 6 of Table 18. A larger amount of coating solution C1 was similarly transferred to a glass slide with various amounts, recorded in line 10 Table 18, to test the effects of drying speed on the coating appearance and morphology. The drug content transfer efficiency of the coating solution was determined to be over 95 percent. This experiment shows that a higher percentage of an organic solvent (acetone) resulted in a clear solution as compared to the stable emulsion from the fourth experiment. However, the coated membrane turned out to be hazy and opaque. This morphology is likely due to a faster drying speed with a higher percentage of acetone in the coating solution, 75 percent, compared to the formulation of the fourth experiment wherein the acetone percentage was 60 percent. The slightly lower acetone concentration led to a slower drying process and a more even and transparent appearance.

In a sixth experiment, an aqueous coating solution using PEG 400, BHT, and PVA as the solubility and transport enhancers was formulated. To a tared 10-ml scintillation vial was added about 100.1 mg of sirolimus (rapamycin, stock # 124623500 batch # RB5070), followed by about 10.1 mg of PEG 400 (Aldrich), and 9.9 mg of BHT (Aldrich) and 9.7 poly(vinyl alcohol) (PVA, 80% hydrolyzed from Aldrich). One point five ml (1.5 ml) of acetone was then added to dissolve the above components under shaking. Once the solution became completely clear, 0.5-ml of water was slowly added to the solution. The mixed solution remained a clear and stable solution at room temperature. The composition of the coating formulation is shown Table 22.

TABLE 22

Aqueous coating formulation using PEG 400, BHT, PVA (C2)

|  | Formulation C2 | Actual am in 2 mL solution |
|---|---|---|
| Sirolimus conc (mg/ml) | 50 | 100.1 |
| PEG 400 | 25 | 10.1 |
| BHT (mg/ml) | 5 | 9.9 |
| PVA (mg/ml) | 5 | 9.7 |
| Acetone (%) | 75 | 1.5 |
| H2O (%) | 25 | 0.5 |

About 100 ul of the clear solution was transferred to a glass slide to form a membrane. The membrane had a weight of 4.8 mg (96 percent transfer efficiency) and formed a smooth and even film. Furthermore, a 3.0×20 mm PTCA balloon was dipped into the coating solution for ten seconds before being pulled out to dry in the laminar hood. The dried weight of the drug coatings are listed in Table 23. The coating appeared to be translucent to clear. The second dip with about five second duration increased the weight by another 2.6 mg and the coating become thicker and more opaque.

TABLE 23

Drug coating weight on balloon surface after dipping coating

|  | Tare weight (g) | wt w/1 coat (g) | Net 1 coat (g) |
|---|---|---|---|
| balloon 1 | 0.0139 | 0.0169 | 0.003 |
| balloon 2 | 0.0159 | 0.0188 | 0.0029 |
| balloon 3 | 0.0471 | 0.0511 | 0.004 |

The coated balloons were then immersed in deionized water (DI water) for two minutes under gentle agitation. The balloons then were clipped to a clamp and placed in a laminar hood to dry for thirty minutes. The coating on the balloons became opaque with a white film on the balloon. On average, the coating lost about 14-54 percent drug coating. The results are listed below in Table 24.

TABLE 24

Loss of coating weight after immersion in water

|  | wt after 1 coat (g) | wt post water soak (g) | wt removed (g) | total coat (g) | % removal |
|---|---|---|---|---|---|
| balloon 1 | 0.0169 | 0.0158 | 0.0011 | 0.0077 | 14.3 |
| balloon 2 | 0.0188 | 0.0165 | 0.0023 | 0.0042 | 54.8 |
| balloon 3 | 0.0511 | 0.0488 | 0.0023 | 0.0077 | 29.9 |

In a seventh experiment, an aqueous coating solution using PEG 400, BHT, PVA and Brij 35 as the solubility and transport enhancers was formulated. To a tared 10-ml scintillation vial was added about 100.0 mg of sirolimus (rapamycin, stock # 124623500 batch # RB5070), followed by about 10.1 mg of PEG 400 (Aldrich), and 9.9 mg of BHT (Aldrich) and 10.1 poly(vinyl alcohol) (PVA, 80 percent hydrolyzed from Aldrich), and 5.7 mg of Brij 35 (Polyoxyethyleneglycol dodecyl ether, a nonionic surfactant, Aldrich). One point five ml (1.2 ml) of acetone was then added to dissolve the above components under shaking. Once the solution became completely clear, 0.8-ml of water was slowly added to the solution. The mixed solution remained a clear and stable solution at room temperature. The composition of the coating formulation is shown in Table 25.

TABLE 25

Aqueous coating formulation using PEG 400, BHT, PVA (B2)

|  | Formulation B2 | Actual am in 2 mL solution |
|---|---|---|
| Sirolimus conc (mg/ml) | 50 | 100.0 |
| PEG 400 | 25 | 10.1 |
| BHT (mg/ml) | 5 | 9.9 |
| PVA (mg/ml) | 5 | 10.1 |
| Brij 35 (mg/ml) | 2.5 | 5.7 |
| Acetone (%) | 60 | 1.2 |
| H2O (%) | 40 | 0.8 |

This coating solution was clear, in contrast to the stable emulsion of B1 from the fourth experiment. This is possibly caused by the addition of PVA and Brij 35 which helps the solubility of sirolimus in the mixed solution. About 100 ul of the clear solution was transferred to a glass slide to form a membrane. The membrane had a weight of 4.6 mg (92 percent transfer efficiency) and formed a smooth and even film. Furthermore, a 3.0×20 mm PTCA balloon was dipped into the coating solution for 10 seconds before being pulled out to dry in the laminar hood. The dried weight of the drug coating was 2.2 mg. The coating appeared to be translucent to clear. The second dip increased the weight by another 3.0 mg and the coating become more opaque. The third dip increased the coating weight by another 3 mg. Also the speed of the dipping is critical in that prolonged exposure to the coating solution will dissolve the previously laid down coating there. The coating weight after each dipping step and final coating weight were listed in Table 26.

TABLE 26

Drug coating weight on balloon surface after dipping coating

|  | tare weight (g) | wt w/1 coat (g) | net 1 coat (g) | wt w/2 coat (g) | net 2 coat (g) | wt w/3 coat (g) | net 3 coat (g) | total coat wt (g) |
|---|---|---|---|---|---|---|---|---|
| balloon 1 | 0.0234 | 0.029 | 0.0056 | 0.0308 | 0.0018 | 0.0311 | 0.0003 | 0.0077 |
| balloon 2 | 0.018 | 0.019 | 0.001 | 0.0196 | 0.0006 | 0.0222 | 0.0026 | 0.0042 |
| balloon 3 | 0.0231 | 0.0255 | 0.0024 | 0.0276 | 0.0021 | 0.0308 | 0.0032 | 0.0077 |

From the study it appears that between 4-7 mg of coating was added to the balloon surface after three dipping steps. The coating appeared to be clear to translucent.

In the final step of the study, the coating balloons were then immersed in deionized water (DI water) for two minutes under gentle agitation. The balloons then clamped to a clip and were placed in a laminar hood to dry for thirty minutes. The coating on the balloons became an opaque and white film on the balloon. On average, the coating lost about 70 percent weight as shown in the Table 27.

TABLE 27

Loss of coating weight after immersion in water

|  | wt after 3 coat (g) | wt post water soak (g) | wt removed (g) | total coat (g) | % removal |
|---|---|---|---|---|---|
| balloon 1 | 0.0311 | 0.0257 | 0.0054 | 0.0077 | 70.1 |
| balloon 2 | 0.0222 | 0.0192 | 0.003 | 0.0042 | 71.4 |
| balloon 3 | 0.0308 | 0.0256 | 0.0052 | 0.0077 | 67.5 |

The loss of coating was probably further facilitated by the additional use of Brij 35 (surfactant) and PVA (water soluble polymer) which hydrate upon contact with water. The amount of Brij 35 and PVA in the final formulation may be adjusted to control the percent of drug release from the balloon surface.

Some of the above listed aqueous formulations are suitable for use as a PTCA balloon surface coating, especially exemplified by formulations B1, B2, C1, and C2. The various excipients may be adjusted to control the coating solution for better stability and ease of detachment from the balloon surface upon deployment.

The formulations, B1 and C1 as listed in Table 18, wherein a good balance of organic solvent such as acetone and water is reached, together with the optional use of excipients such as PEG, PVA and BHT may be used to control separation of the drug coating from the balloon surface. These excipients, by their amphiphilic nature (PEG, Brij 35, and PVA) should also facilitate the transport of drug into the tissue and enhance their tissue retention as well. An additional detachment facilitating agent such as PVA and non-ionic surfactant (Brij 35) as used in the formulation set forth in Table 22 for C2, and table 23 for B2 also helped separate the drug coating from the balloon surface.

Accordingly, Table 28 below lists the preferred formulation ranges for surface coatings based upon the individual formulations B1, B2, C1 and C2 described above.

TABLE 28

Formulation summary

|  | B1 | C1 | B2 | C2 |
|---|---|---|---|---|
| Sirolimus conc (mg/ml) | 50 | 50 | 50 | 50 |
| PEG 400 (mg/ml) | 5 | 5 | 5 | 5 |
| BHT (mg/ml) | 5 | 5 | 5 | 5 |
| Brij 35 (mg/ml) | N/A | N/A | 2.5 | 2.5 |
| Acetone/H2O | 60/40 | 75/25 | 60/40 | 75/25 |

Figure 2A:
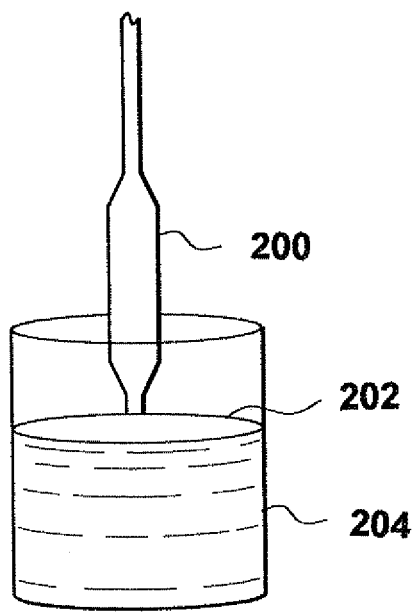
FIGS. 2A and 2B illustrate a dip coating process of a PTCA balloon in a liquid formulation of a therapeutic agent in accordance with the present invention.
Figure 2B:
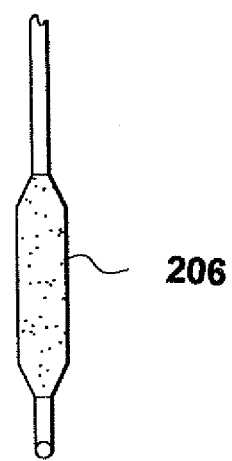

It is important to note that the balloon or other medical device may be coated in any suitable manner. For example, the balloon may be spray coated, have the coating brushed or wiped on, or dip coated. FIG. 2A illustrates a balloon 200 being dipped into a coating solution, suspension and/or emulsion 202 contained within a vial 204 and FIG. 2B illustrates the coated balloon 206. This process, as described herein, may be repeated multiple times to achieve the desired drug concentration.

It is important to note that when utilizing a balloon or other expandable member to deliver drugs and/or therapeutic agents, the balloon or other expandable member is expanded to a diameter at least ten percent higher than the nominal diameter of the vessel. This over expansion serves a number of functions, including facilitation of the drug and/or therapeutic agent into the surrounding tissues. Furthermore, the level and duration of inflation or expansion may influence the extent of drug uptake in the target tissue.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A medical device comprising: an expandable member having a first diameter for insertion into a vessel and a second diameter for making contact with the vessel walls; and a liquid formulation of a rapamycin affixed to at least a portion of the surface of the expandable member, the liquid formulation of a rapamycin comprising about 50 mg/ml of a rapamycin, about 5 mg/ml of a first excipient selected from the group of polymers consisting of PEG 400, PEG 1000, PEG 1500, PEG 2000 and polyvinyl alcohol, about 5 mg/ml of a second excipient selected from the group of antioxidants consisting of BHT, BHA and vitamin E TPGS, ascorbyl palmitate, and resveratrol, and acetone and water in a ratio of about 60/40 to about 75/25.

2. The medical device according to claim 1 further comprising about 2.5 mg/ml of a third excipient selected from the group of non-ionic surfactants consisting of polyoxyethylene lauryl ether, polyoxyethylene (20) sorbitan monolaurate, polyoxyethylene (20) sorbitan monooleate, octylphenol ethoxylates, lauryl myristate, and lauryl palmitate.

3. The medical device according to claim 1, wherein the expandable member comprises a balloon.

4. The medical device according to claim 1, wherein the liquid formulation is dried to a non-solvent containing composition to modify the surface of the expandable member.

5. A method for coating a device comprising: making a liquid formulation of a rapamycin comprising about 50 mg/ml of a rapamycin, about 5 mg/ml of a first excipient selected from the group of polymers consisting of PEG 400, PEG 100, PEG 1500, PEG 2000 and polyvinyl alcohol, about 5 mg/ml of a second excipient selected from the group of antioxidants consisting of BHT, BHA and vitamin E TPGS, ascorbyl palmitate, and resveratrol, and acetone and water in a ratio of about 60/40 to about 75/25;
coating an expandable device with the liquid formulation for less than 10 seconds;
drying the coated expandable device for about 10 minutes;
recoating the expandable device with the liquid formulation for less than 5 seconds; and
drying the recoated expandable device for about 10 minutes.

6. The method for coating a device according to claim 5, wherein the step of making the liquid formulation further comprises adding a third excipient selected from the group consisting of polyoxyethylene lauryl ether, polyoxyethylene (20) sorbitan monolaurate, polyoxyethylene (20) sorbitan monooleate, octylphenol ethoxylates, lauryl myristate, and lauryl palmitate.

7. A liquid formulation of a rapamycin comprising about 50 mg/ml of a rapamycin, about 50 mg/ml of a first excipient selected from the group of polymers consisting of PEG 400, PEG 1000, PEG 1500, PEG 2000 and polyvinyl alcohol, about 5 mg/ml of a second excipient selected from the group of antioxidants consisting of BHT, BHA and vitamin E TPGS, ascorbyl palmitate, resveratrol, and acetone arid water in a ratio of about 60/40 to about 75/25.

8. The liquid formulation of a rapamycin according to claim 7 further comprising a third excipient selected from the group of non-ionic surfactants consisting of polyoxyethylene lauryl ether, polyoxyethylene (20) sorbitan monolaurate, polyoxyethylene (20) sorbitan monooleate, octylphenol ethoxylates, lauryl myristate, and lauryl palmitate.

9. A method for the treatment of vascular disease comprising: positioning an expandable member having a first unexpanded diameter proximate a treatment site of a diseased vessel; and
expanding the expandable member to a second diameter such that it makes contact with the vessel walls at the treatment site, the expandable member having a coating comprising about 50 mg/ml of a rapamycin, about 5 mg/ml of a first excipient selected from the group of polymers consisting of PEG 400, PEG 100, PEG 1500, PEG 2000 and polyvinyl alcohol, about 5 mg/ml of a second excipient selected from the group of antioxidants consisting of BHT, BHA and vitamin E TPGS, ascorbyl palmitate, and resveratrol, and acetone and water in a ratio of about 60/40 to about 75/25, wherein the expansion of the expandable member to its second diameter facilitates the uptake of the liquid formulation into the tissues comprising the vessel walls.

10. The liquid formulation of a rapamycin according to claim 9 further comprising a third excipient selected from the group of non-ionic surfactants consisting of polyoxyethylene lauryl ether, polyoxyethylene (20) sorbitan monolaurate, polyoxyethylene (20) sorbitan monooleate, octylphenol ethoxylates, lauryl myristate, and lauryl palmitate.

11. The expandable member of the medical device in claim 9 is expanded to a final diameter at the treatment site that is larger than the nominal diameter of the artery by at least 10 percent.

* * * * *